United States Patent
Bae et al.

(10) Patent No.: US 7,678,474 B2
(45) Date of Patent: Mar. 16, 2010

(54) IMIDAZOLE DERIVATIVES AND ORGANIC ELECTRONIC DEVICE USING THE SAME

(75) Inventors: Jae Soon Bae, Daejeon Metropolitan (KR); Dae Woong Lee, Daejeon Metropolitan (KR); Dong Hoon Lee, Seoul (KR); Dong Seob Jeong, Seoul (KR)

(73) Assignee: LG Chem. Ltd., Seoul (KR)

( * ) Notice: Subject to any disclaimer, the term of this patent is extended or adjusted under 35 U.S.C. 154(b) by 753 days.

(21) Appl. No.: 11/487,988

(22) Filed: Jul. 18, 2006

(65) Prior Publication Data

US 2007/0018154 A1    Jan. 25, 2007

(30) Foreign Application Priority Data

Jul. 22, 2005   (KR) ............... 10-2005-0066731

(51) Int. Cl.
| | |
|---|---|
| H01L 51/54 | (2006.01) |
| H01L 51/46 | (2006.01) |
| H05B 33/12 | (2006.01) |
| C07D 235/02 | (2006.01) |
| C07D 403/00 | (2006.01) |
| C07D 417/00 | (2006.01) |
| C07D 409/00 | (2006.01) |

(52) U.S. Cl. ............... 428/690; 428/917; 313/504; 313/506; 257/40; 136/263; 548/301.7; 548/311.4; 548/311.1

(58) Field of Classification Search ............... None
See application file for complete search history.

(56) References Cited

U.S. PATENT DOCUMENTS 6,200,984 B1 *  3/2001  Reitz et al. ............... 514/285

FOREIGN PATENT DOCUMENTS

| EP | 0 763 965 A2 | 3/1997 |
|---|---|---|
| JP | 63-172166 | * 7/1988 |
| JP | 04-174856 | * 6/1992 |
| JP | 04-296761 | * 10/1992 |
| JP | 09-073181 | * 3/1997 |
| JP | 09-241255 | 9/1997 |
| JP | 10-265478 | 10/1998 |
| JP | 2004-075603 | 3/2004 |
| JP | 2004-349245 | 12/2004 |

OTHER PUBLICATIONS

El-Shafei et al., Heterocycles, vol. 19, No. 2, (1982), pp. 333-338.*
Truitt et al., Journal of the American Chemical Society, (1957), vol. 79, pp. 5708-5710.*
Maryanoff et al., Bioorganic and Medicinal Chemistry Letters, vol. 9, No. 11, (1999), pp. 1547-1552.*

* cited by examiner

*Primary Examiner*—Dawn Garrett
(74) *Attorney, Agent, or Firm*—McKenna Long & Aldridge LLP

(57) ABSTRACT

Disclosed herein are novel imidazole derivatives and organic electronic device using the same. The disclosed organic electronic device show excellent characteristics in terms of efficiency, driving voltage and stability.

12 Claims, 4 Drawing Sheets

IMIDAZOLE DERIVATIVES AND ORGANIC ELECTRONIC DEVICE USING THE SAME

TECHNIAL FIELD

The present invention relates to imidazole derivatives having novel structures, and organic electronic device using the same.

This application claims the benefit of the filing date of Korean Patent Application Nos. 10-2005-0066731, filed on 2005 Jul. 22, with the Korean Intellectual Property Office, the disclosure of which is incorporated herein in its entirety by reference.

BACKGROUND ART

As used herein, the term "organic electronic devices" refers to devices wherein charge exchange between electrodes and organic layers occurs using holes and/or electrons. The organic electronic devices can be broadly divided, according to the operating principle, into the following two groups. The first group includes electronic devices in which excitons are formed in an organic layer by photons from an external light source introduced into the devices, and are separated into electrons and holes, which are then transferred to different electrodes so as to be used as current sources (voltage sources). The second group includes electronic devices in which voltage or current is applied to at least two electrodes to inject holes and/or electrons into an organic semiconductor forming an interface with the electrodes, such that the devices operate using the injected electrons and holes.

Examples of the organic electronic devices include organic light-emitting devices, organic solar cells, organic photoconductor (OPC) drums, and organic transistors, all of which require a hole injection or transport material, an electron injection or transport material, or a light emitting material for driving thereof. A description will be given below mainly of organic light-emitting devices, however, the principle of action of the hole injection or transport material, the electron injection or transport material, and the light-emitting material is similar between organic electronic devices.

In general, an organic light-emitting phenomenon is a phenomenon in which electrical energy is transformed into light energy by means of an organic material. The organic light-emitting device employing the organic light-emitting phenomenon generally has a structure comprising an anode, a cathode and an organic layer interposed therebetween. Herein, the organic layer frequently consists of a structure of a plurality of layers made of different materials in order to increase the efficiency and stability of the organic light-emitting device. For example, it may consist of a hole injection layer, a hole transport layer, a light-emitting layer, an electron transport layer, an electron injection layer and the like. In this structure of the organic light-emitting device, when voltage is applied between the two electrodes, holes and electrons are injected into the organic layer from the anode and the cathode, respectively. When the holes and electrons injected as described above are recombined, excitons are formed. When the excitons drop to a ground state, light is emitted. This organic light-emitting device is known to have various characteristics, including spontaneous emission, high brightness, high efficiency, low driving voltage, wide viewing angle, high contrast, and high-speed response characteristics.

Materials for forming the organic layer in the organic light-emitting device can be divided, according to function, into light-emitting materials and charge transport materials, for examples, hole injection materials, hole transport materials, electron transport materials, electron injection materials and the like. Also, light-emitting materials can be divided, according to the color of light emission, into blue, green and red light-emitting materials, and yellow and orange light-emitting materials required for exhibiting more natural colors. Meanwhile, if only one material is used as light-emitting material, there occur problems in that the peak emission wavelength shifts to a long wavelength due to the interaction between molecules, thereby reducing color purity, or the efficiency of the device is reduced due to a quenching effect. For this reason, in order to improve color purity and to increase light emission efficiency through energy transfer, a host/dopant system can be used as a light-emitting material.

In order for the organic light-emitting device to sufficiently exhibit the above-described excellent characteristics, materials forming the organic layer in the device (e.g., a hole injection material, a hole transport material, a light-emitting material, an electron transport material, an electron injection material, etc.) must be stable and efficient materials. However, the development of efficient organic layer materials for the organic light-emitting devices is not yet sufficient, and thus there remains a need for the development of new materials. There is also the need to develop these materials for other organic electronic devices.

[Disclosure]

[Technical Problem]

The present inventors have discovered imidazole derivatives having new structures and found that these compounds can perform the role of hole injection, hole transport, electron injection, electron transport and/or light emission in organic electronic devices, including organic light-emitting devices.

Thus, it is an object of the present invention to provide imidazole derivatives having novel structures and organic electronic device using the same.

[Technical Solution]

The present invention provides an organic electronic device comprising a first electrode, a second electrode and one or more organic layers disposed between the first and second electrodes, in which at least one layer of the organic layers comprises a compound represented by Formula 1:

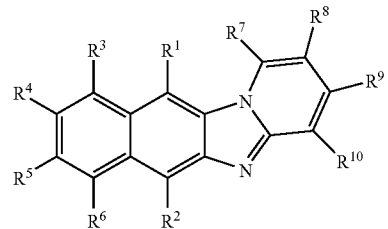

[Formula 1]

wherein $R^1$ to $R^{10}$ are each independently or together selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted alicyclic group, a substituted or unsubstituted silicon group, a substituted or unsubstituted boron group, an amino group, a nitrile group, a nitro group, a halogen group, an amide group, and an ester group, wherein two substituents adjacent to each other may form an alicyclic or heterocyclic ring together.

Also, the present invention provides imidazole derivatives represented by Formula 2:

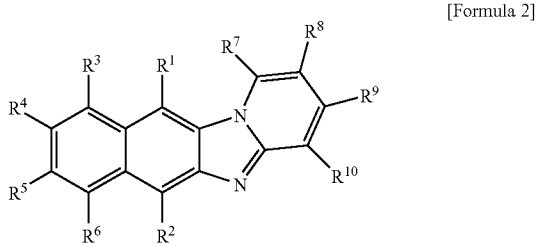

[Formula 2]

wherein $R^1$ to $R^{10}$ are each independently or together selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted alicyclic group, a substituted or unsubstituted silicon group, a substituted or unsubstituted boron group, an amino group, a nitrile group, a nitro group, a halogen group, an amide group, and an ester group, wherein two substituents adjacent to each other may form an alicyclic or heterocyclic ring together, provided that all of $R_1$ to $R^{10}$ are not simultaneously hydrogen.

Hereinafter, the present invention will be described in detail.

For description, the steric structure of the compound of Formula 1 can be divided into moieties A and B as shown in the following figure.

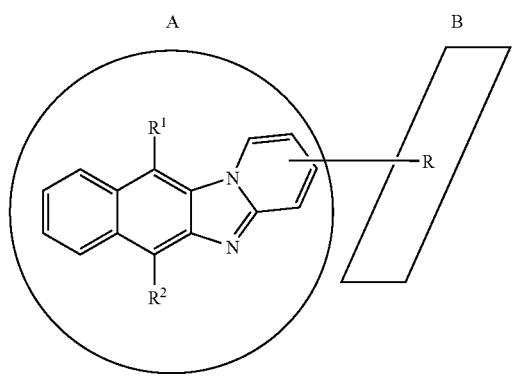

The moiety A, in which a naphthalene group forms a fused ring with an imidazole group, has a generally planar structure, like an anthracene structure, while showing blue emission. Typically, in the case of a compound in which each of $R^1$ and $R^2$ in Formula 1 is a 2-naphthyl group and R in the moiety B is hydrogen, i.e., a compound containing five-membered aromatic heterocycles, which are one more than those of anthracene, the compound had a maximum absorption wavelength ($_{max}$) of 360 nm and a band gap of 2.95 eV. From this fact, the core represented by the moiety A can be expected to have a blue emission band slightly shifted to the long wavelength region compared to anthracene.

It is known that the imidazole group is frequently used as a substituent group of an electron injection and/or transport material or a light-emitting material in organic light-emitting devices, and has an important effect on electron injection or transport or light emission. Thus, because the moiety A of the compound of Formula 1, which has a structure forming a fused ring with an imidazole group, still has the nature of the imidazole group, it has the n-type nature, in which electron injection and transfer is easy. As used herein, the term "n-type nature" generally refers to a conductive property according to the LUMO level, and thus an anionic property resulting from the formation of electrons.

For example, a compound, in which $R^1$ and $R^2$ in the structure of Formula 1 are substituted with a 2-naphthyl group and R is hydrogen, was measured to have a HOMO value of 5.8-6.0 eV, which corresponds to a relatively low energy level. Also, the LUMO value of the compound was measured to be 2.9-3.1 eV. Such HOMO and LUMO values shows that the compound can perform electron transport in organic light-emitting devices, and when used as the material of an electron transport layer, it can also perform the role of hole-blocking that prevents holes injected and transported from a hole injection layer and hole transport layer from being injected into a cathode located at the opposite side so as to reduce the stability of the devices.

Moreover, $R^1$ to $R^{10}$ in the structure of Formula 1 can be introduced with various substituents. Thus, the energy level or energy band gap of the compound of Formula 1 can be variously controlled to various levels by introducing into the structure of Formula 1 an arylamine substituent that is resistant to holes, or a substituent having a suitably controlled conjugation length. The compound of Formula 1, which has an energy level controlled by the introduction of such various substituents, can be used not only as electron injection and transport materials, but also as hole injection, hole transport and light-emitting materials. In the present invention, among the compounds of Formula 1, compounds having suitable energy levels according to substituents are selected and used in organic electronic devices, including organic light-emitting devices, and thus devices having low driving voltage and high light efficiency can be realized.

Also, because $R^1$ to $R^{10}$ in Formula 1 are introduced with various substituents, the pi-pi interaction in the compound structure can be reduced to suppress excimer or exciplex formation, which occurs in materials having a planar structure.

Hereinafter, the substituents in Formula 1 or Formula 2 will be described in detail.

The alkyl group, alkoxy group and alkenyl group of $R^1$ to $R^{10}$ in Formula 1 or Formula 2 preferably have 1 to 30 carbon atoms.

Examples of the aryl group of $R^1$ to $R^{10}$ in Formula 1 or Formula 2 include a phenyl group, naphthyl group, anthranyl group, biphenyl group, pyrenyl group and perylene group, but are not limited thereto.

Example of the arylamine group of $R^1$ to $R^{10}$ in Formula 1 or Formula 2 include a diphenylamine group, phenylnaphthylamine group, ditolylamine group, phenyltolylamine group, carbazole group and triphenylamine group, but are not limited thereto.

Examples of the heterocyclic group of $R^1$ to $R^{10}$ in Formula 1 or Formula 2 include a pyridyl group, a bipyridyl group, acridyl group, thiophene group, imidazole group, oxazole group, thiazole group and quinolinyl group, but are not limited thereto.

Examples of the halogen group of $R^1$ to $R^{10}$ in Formula 1 or Formula 2 include fluorine, chlorine, bromine and iodine.

In the present invention, when $R^1$ to $R^{10}$ in Formula 1 or Formula 2 are substituted with other substituents, these substituents are preferably selected from the group consisting of an alkyl group, alkenyl group, aryl group, arylamine group, heterocyclic group and alicyclic group. When the compounds of Formula 1 or 2 have the above-described substituents, the physical properties of the above-described core structure do not change depending on the kind of substituent.

In Formula 1 and Formula 2, preferably, $R^1$ and $R^2$ are not simultaneously hydrogen, and are each independently selected from hydrogen, a substituted or unsubstituted alkenyl group, a substituted or unsubstituted aryl group, a substituted or unsubstituted arylamine group, and a substituted or unsubstituted heterocyclic group, $R^3$ to $R^6$ are each independently selected from the group consisting of hydrogen, a nitrile group, a substituted or unsubstituted aryl group, a substituted or unsubstituted arylamine group, and a substituted or unsubstituted heterocyclic group, and $R^7$ to $R^{10}$ are each independently selected from the group consisting of hydrogen, a nitrile group, an alkyl group, a substituted or unsubstituted alkenyl group, a substituted or unsubstituted aryl group, a substituted or unsubstituted arylamine group, and a substituted or unsubstituted heterocyclic group.

More preferably, $R^1$ and $R^2$ in Formula 1 or Formula 2 are selected from the group consisting of an alkenyl group, aryl group, arylamine group and heterocyclic group, $R^3$ to $R^6$ are hydrogen, and $R^7$ to $R^{10}$ are selected from the group consisting of hydrogen, a nitrile group, alkyl group, alkenyl group, aryl group, arylamine group and heterocyclic group.

Specific examples of the compounds of Formula 1 or 2 include compounds represented by the following formulas, but the scope of the present invention is not limited only to these compounds.

[Formula 1-1]

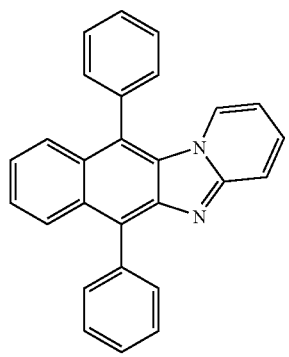

[Formula 1-2]

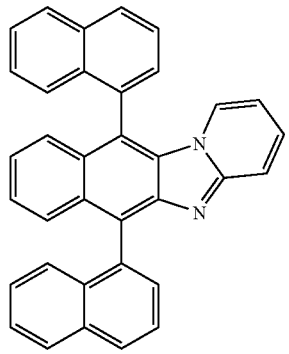

[Formula 1-3]

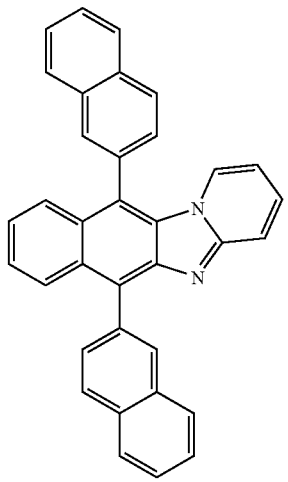

[Formula 1-4]

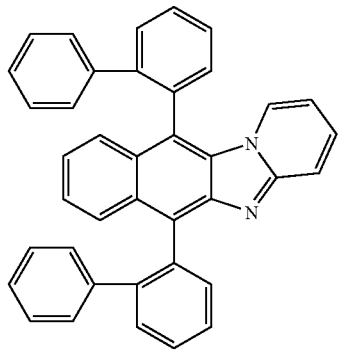

[Formula 1-5]

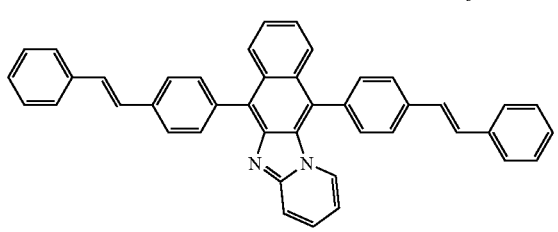

[Formula 1-6]

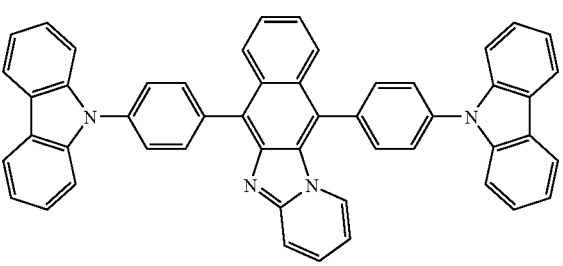

-continued
[Formula 1-7]
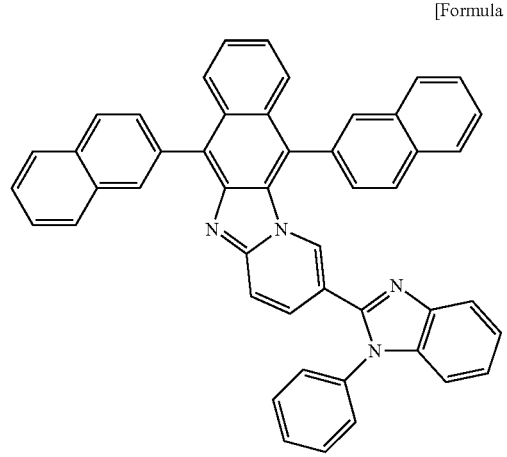
[Formula 1-8]
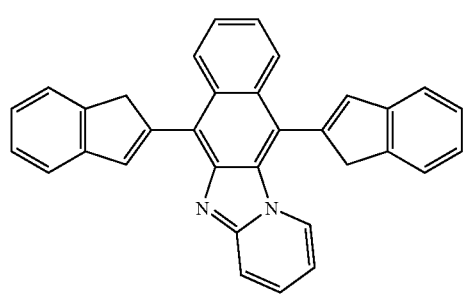
[Formula 1-9]
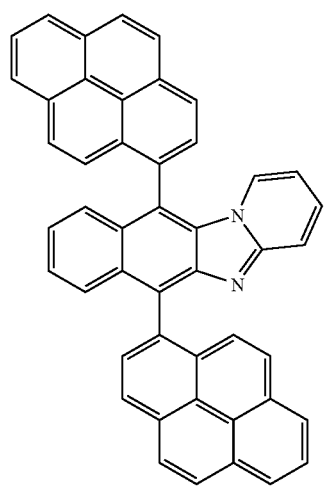
[Formula 1-10]
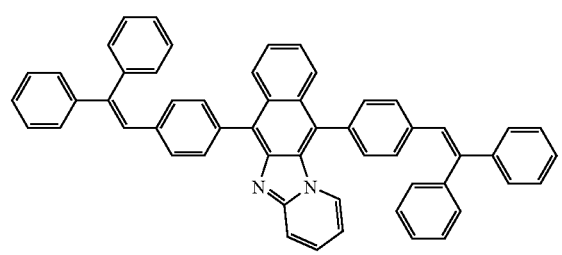
[Formula 1-11]
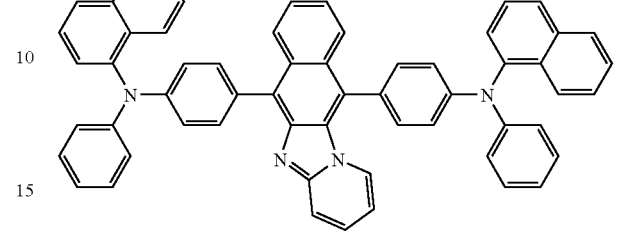
[Formula 1-12]
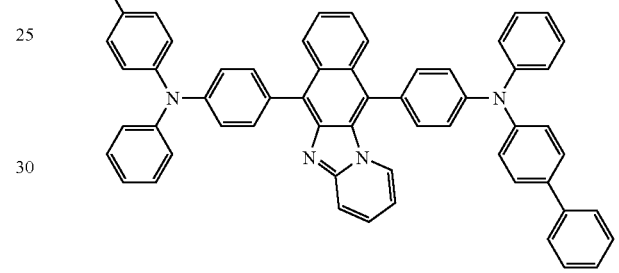
[Formula 1-13]
[Formula 1-14]
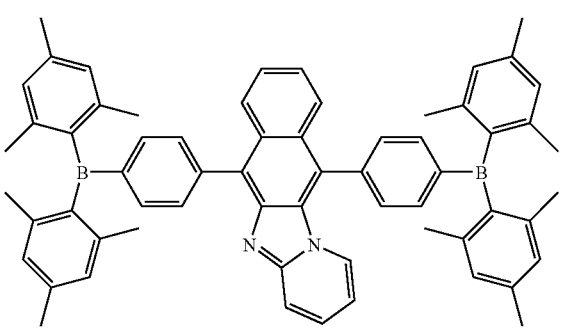

[Formula 1-15]
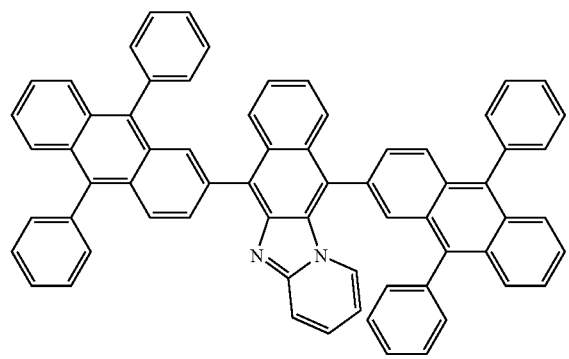
[Formula 1-16]
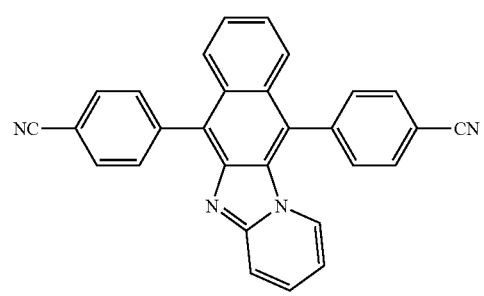
[Formula 1-17]
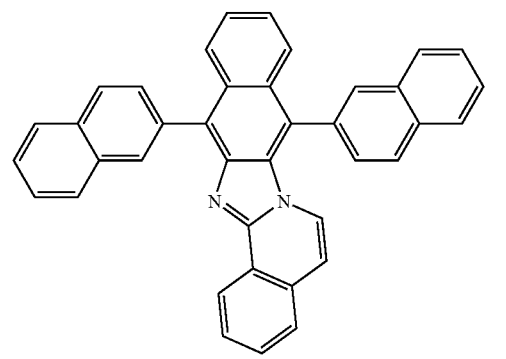
[Formula 1-18]
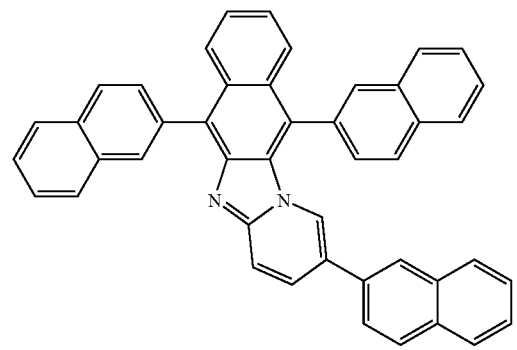
[Formula 1-19]
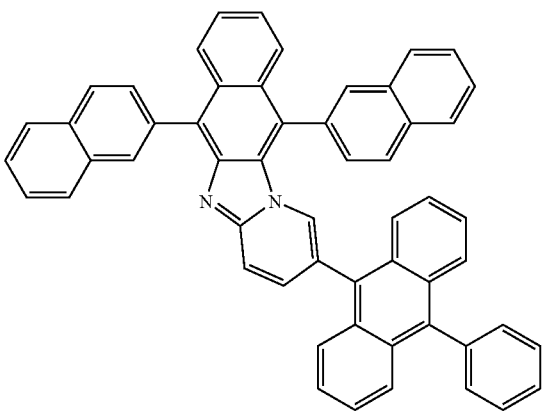
[Formula 1-20]
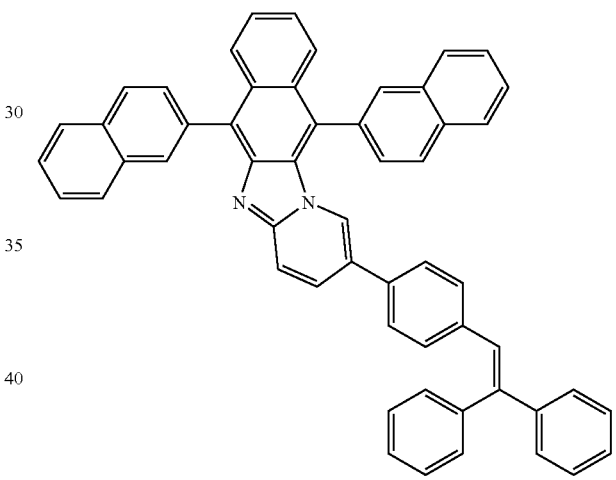
[Formula 1-21]
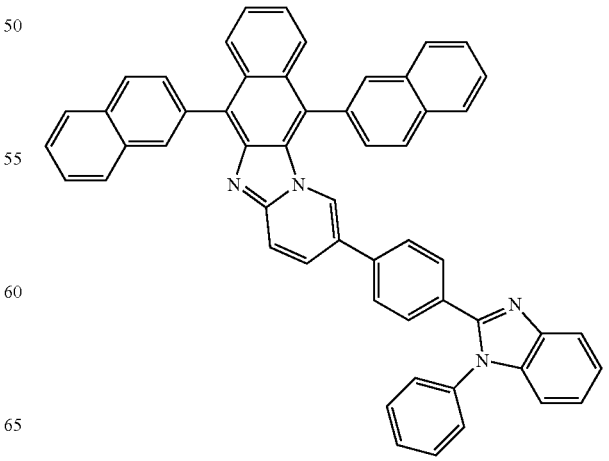

-continued
[Formula 1-22]
[Formula 1-23]
[Formula 1-24]
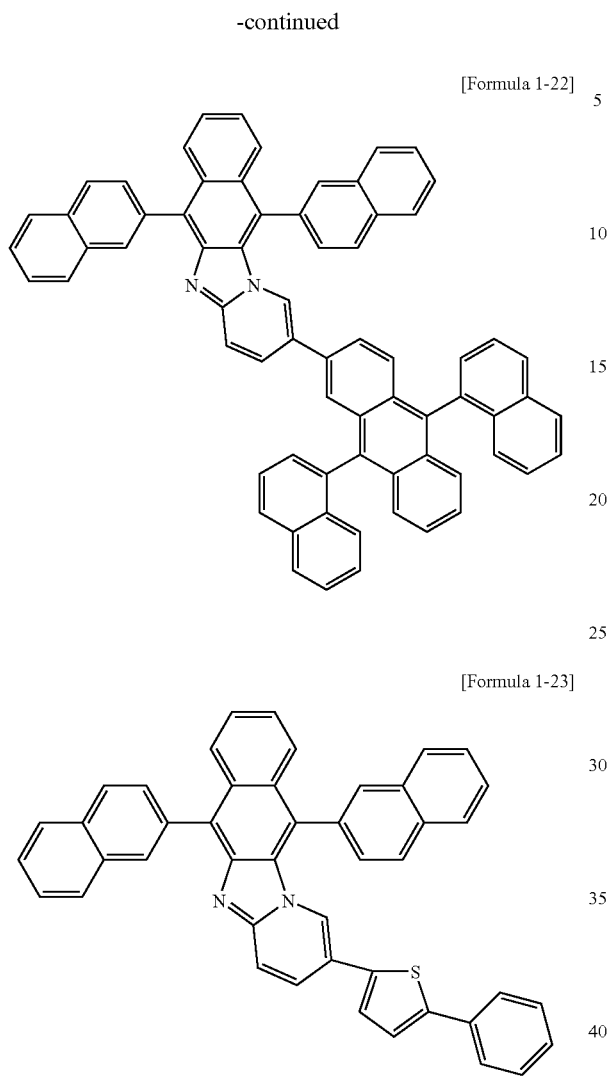
-continued
[Formula 1-25]
[Formula 1-26]
[Formula 1-27]
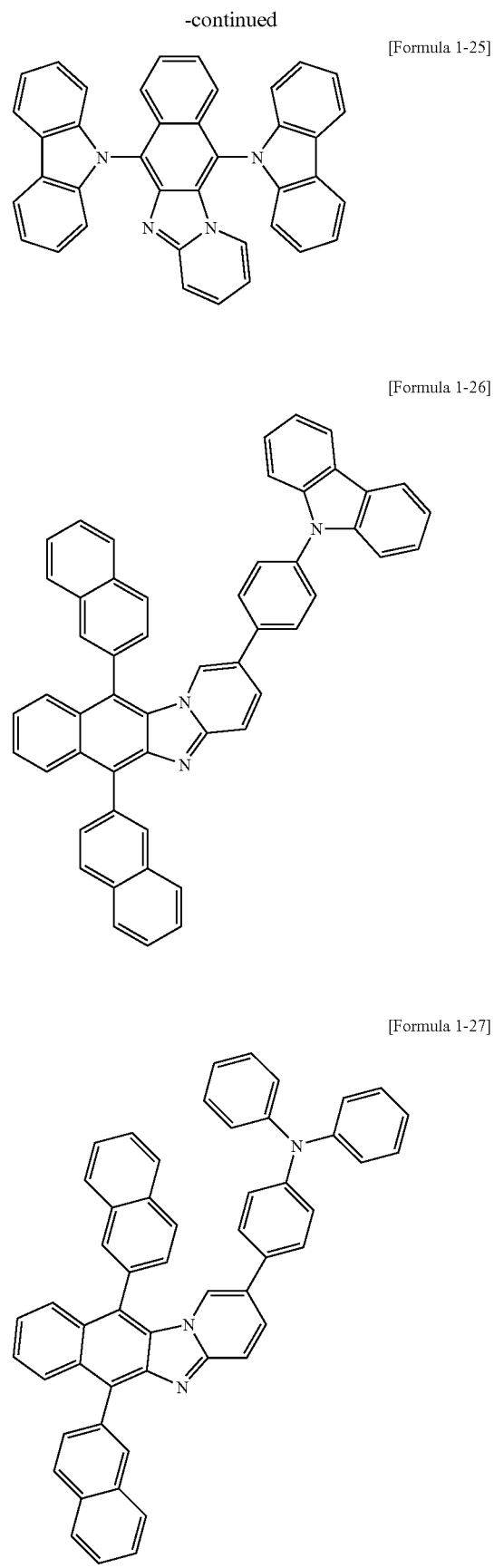

-continued
[Formula 1-28]
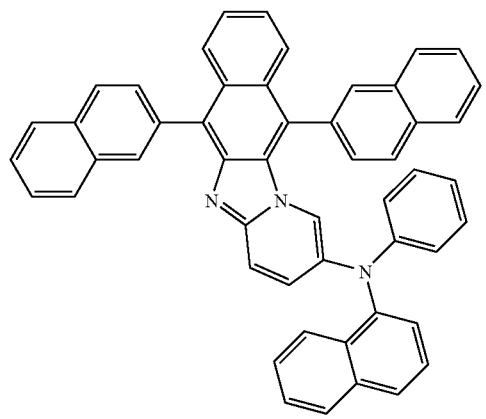
[Formula 1-29]
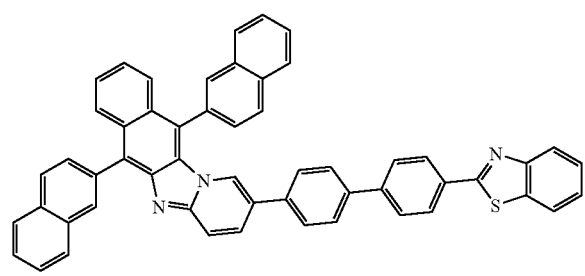
[Formula 1-30]
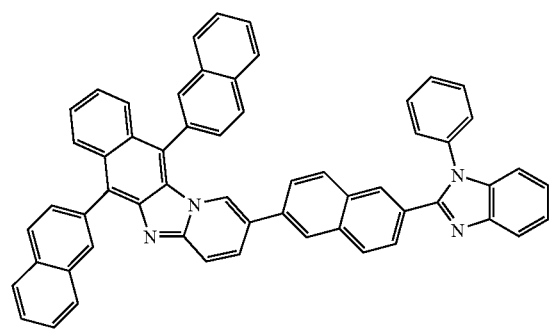
[Formula 1-31]
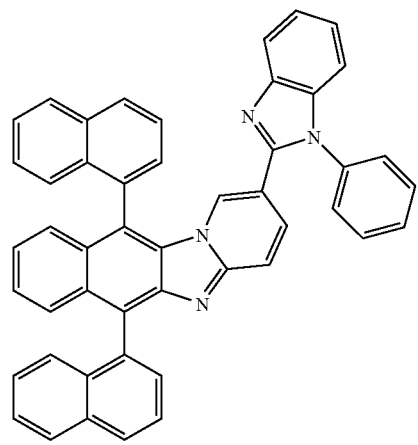
-continued
[Formula 1-32]
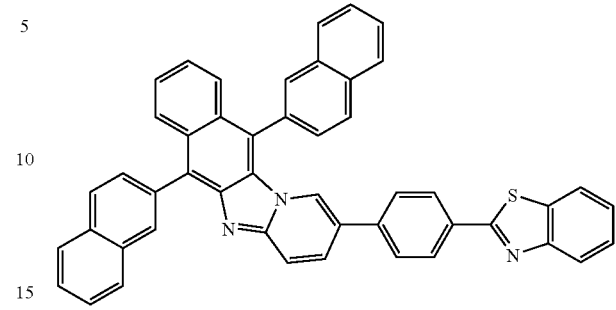
[Formula 1-33]
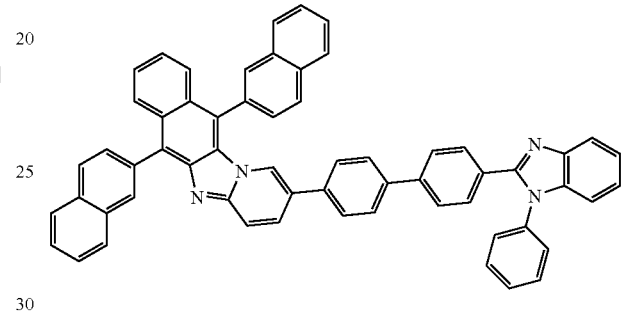
[Formula 1-34]
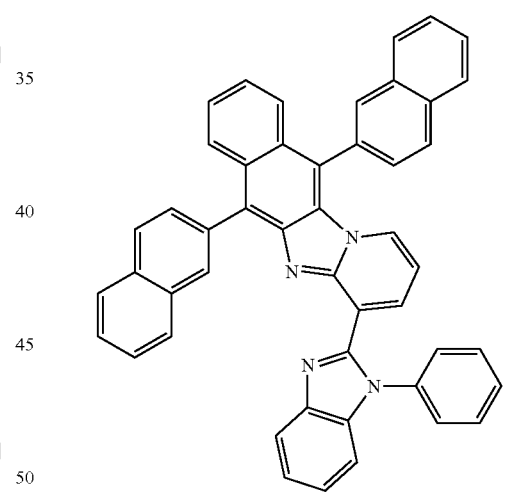
[Formula 1-35]
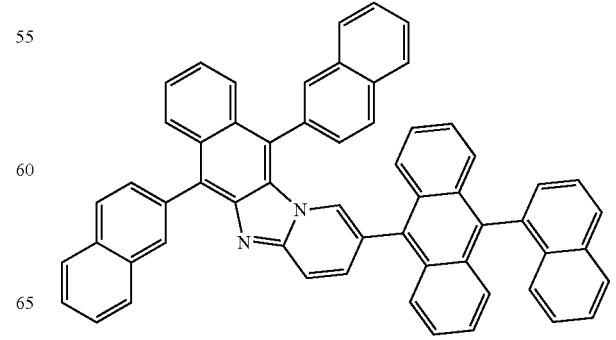

[Formula 1-36]
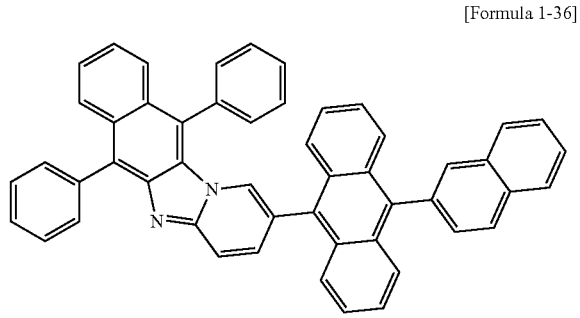
[Formula 1-39]
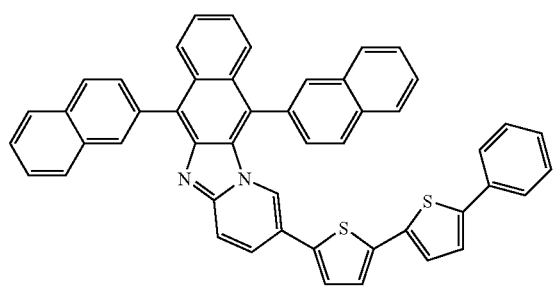
[Formula 1-37]
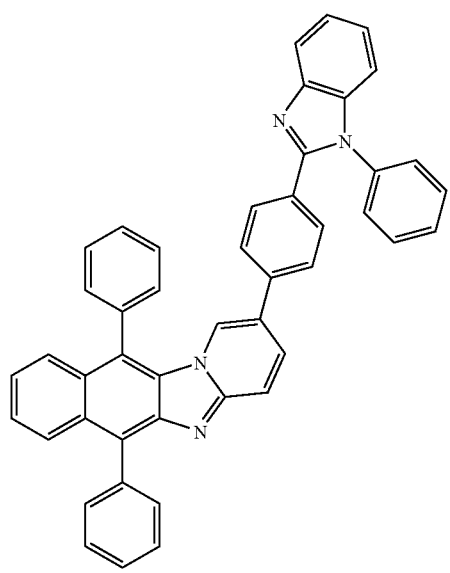
[Formula 1-40]
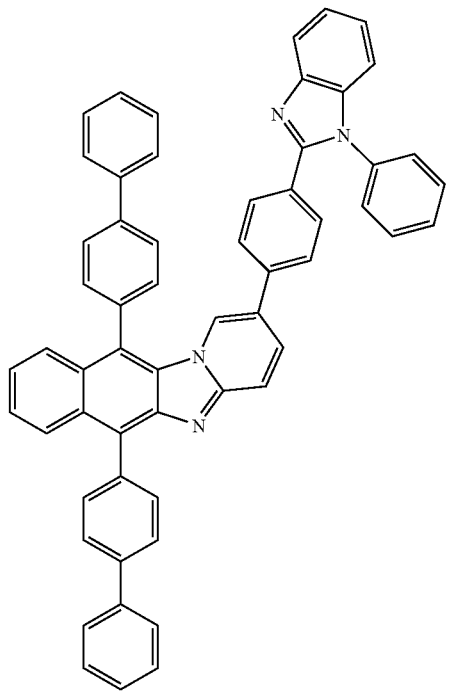
[Formula 1-38]
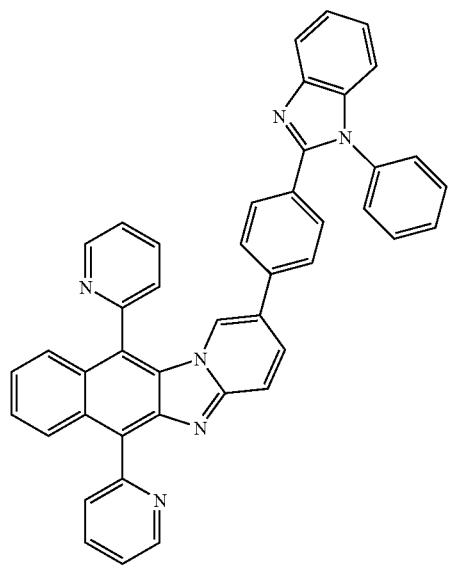
[Formula 1-41]
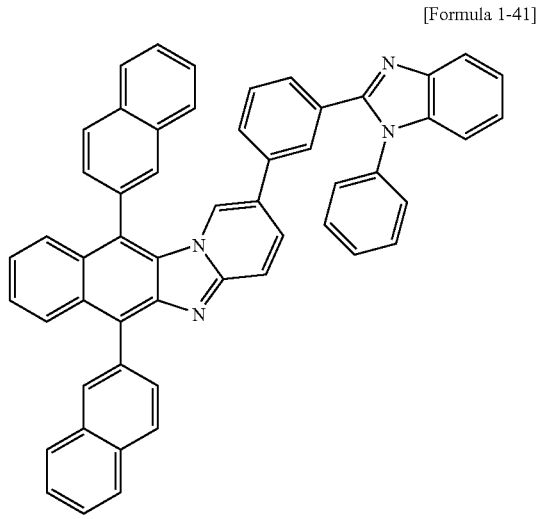

[Formula 1-42]
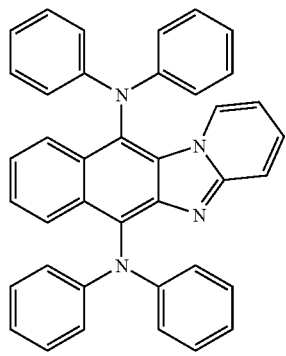
[Formula 1-43]
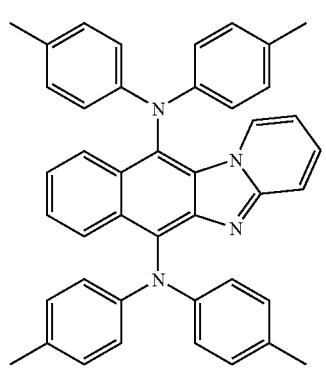
[Formula 1-44]
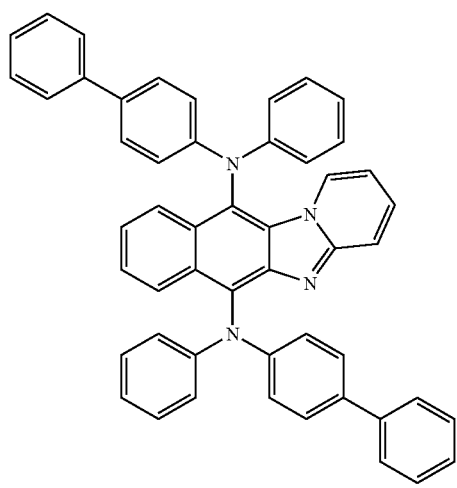
[Formula 1-45]
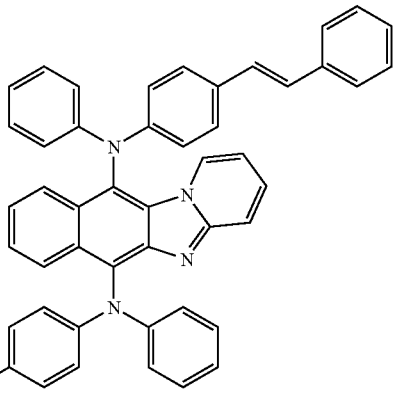
[Formula 1-46]
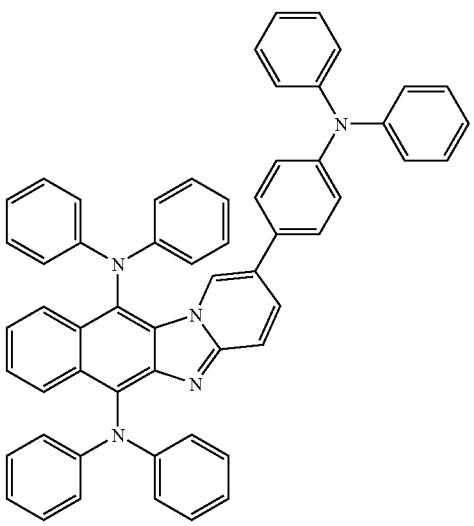
[Formula 1-47]
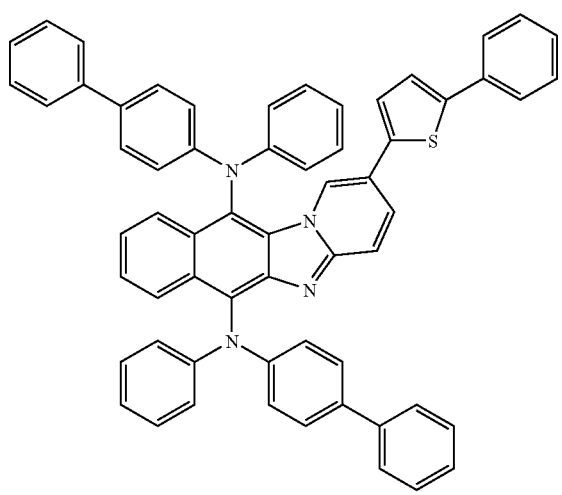
The above-described compounds according to the present invention can be prepared in the following manner.
For example, the compounds of Formula 1 or Formula 2 can be prepared using a method comprising the steps of:

a) allowing substituted or unsubstituted 2,3-dihalogen-1,4-naphthoquinone to react with substituted or unsubstituted ortho-aminopyridine derivatives;

b) converting the ketone group of the compounds obtained in said step a) into alcohol so as to prepare dialcohol compounds; and c) reducing the dialcohol compounds obtained in said step b) to produce a naphthalene group in the compounds.

In another embodiment, the compounds of Formula 1 or Formula 2 can be prepared using a method comprising the steps of:

a) allowing substituted or unsubstituted 2,3-dihalogen-1,4-naphthoquinone to react with substituted or unsubstituted ortho-aminopyridine derivatives;

b) reducing the naphthoquinone group of the compounds obtained in said step a) to produce a naphthalene group;

c) introducing bromine (Br) into each of positions to be substituted with $R^1$ and $R^2$ in the compounds obtained in said step b); and d) using boronic acid or borate to introduce substituents into the positions introduced with the bromo group in the compounds obtained in said step c).

In said method, the bromine introduction step c) can be carried out by allowing the compounds to react with NBS (N-bromosuccinimide) or $Br_2$ in the presence of a solvent such as chloroform, acetic acid or DMF (dimethylformamide).

Hereinafter, the method for preparing the compounds of Formula 1 or Formula 2 will be described in further detail.

In one embodiment, the inventive compounds can be prepared in the following manner according to Reaction Scheme 1. As starting materials, substituted or unsubstituted 2,3-dichloro or dibromo 1,4-naphthoquinone and substituted or unsubstituted ortho-aminopyridine compounds can be used. The substituted or unsubstituted ortho-aminopyridine compounds may be, for example, compounds represented by the following formulas, but are not limited thereto:

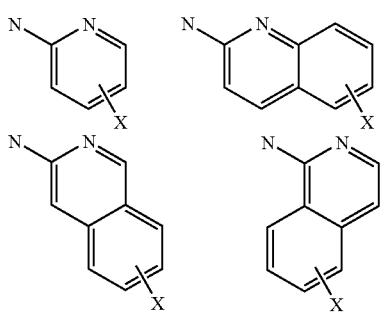

wherein X is selected from the group consisting of hydrogen, a substituted or unsubstituted alkyl group, substituted or unsubstituted alkoxy group, substituted or unsubstituted alkenyl group, substituted or unsubstituted aryl group, substituted or unsubstituted arylamine group, substituted or unsubstituted heterocyclic group, substituted or unsubstituted alicyclic group, substituted or unsubstituted silicon group, substituted or unsubstituted boron group, amino group, nitrile group, nitro group, halogen group, amide group, and ester group. X may be at least two in number, in which case these substituents can be different from each other.

Using said starting materials, compound B can be prepared according to Reaction Scheme 1 below.

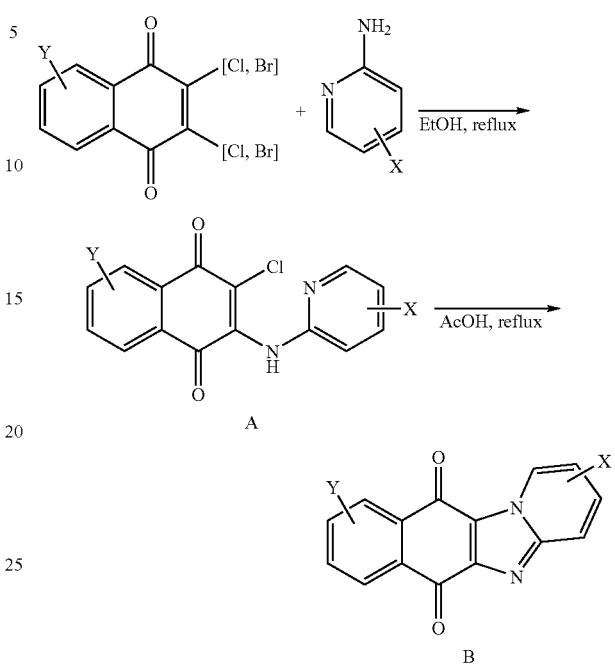

[Reaction Scheme 1]

wherein X and Y are each independently selected from the group consisting of hydrogen, a substituted or unsubstituted alkyl group, substituted or unsubstituted alkoxy group, substituted or unsubstituted alkenyl group, substituted or unsubstituted aryl group, substituted or unsubstituted arylamine group, substituted or unsubstituted heterocyclic group, substituted or unsubstituted alicyclic group, substituted or unsubstituted silicon group, substituted or unsubstituted boron group, amino group, nitrile group, nitro group, halogen group, amide group, and ester group. Each of said X and Y may be at least two in number, in which case these substituents X or Y can be different from each other.

Then, an $R^1$ or $R^2$ substituent having a bromo group may be allowed to react with said compound B in the presence of t-BuLi or n-BuLi and THF so as to prepare a dialcohol compound having the $R^1$ and $R^2$ substituents. Then, this compound may be allowed to react in KI, $NaH_2PO_2.H_2O$ and acetic acid so as to prepare the compound of Formula 1, having the $R^1$ and $R^2$ substituents. This reaction can be represented by, for example, Reaction Scheme 2 below.

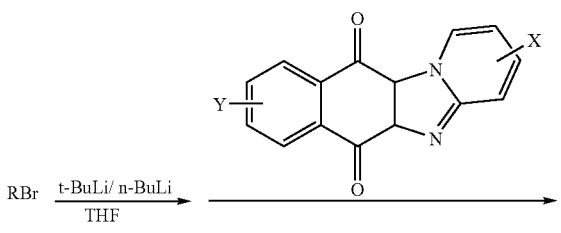

[Reaction Scheme 2]

-continued

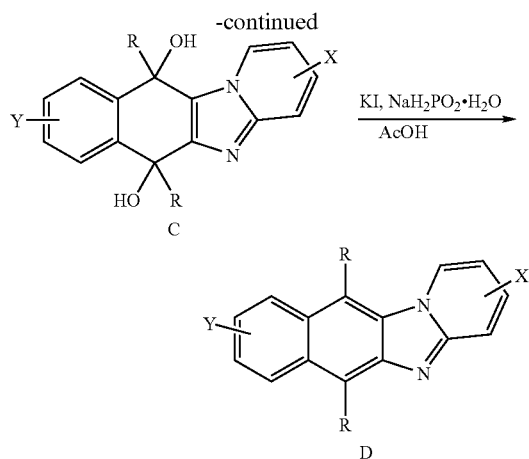

C

D

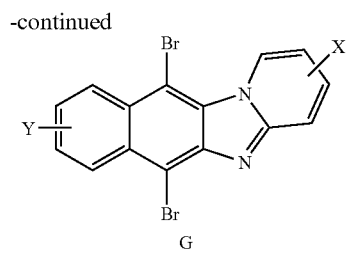

G wherein X and Y have the same meanings as defined above for Reaction Scheme 1.

Meanwhile, a boronate compound E can be prepared according to Reaction Scheme 4:

[Reaction Scheme 4]

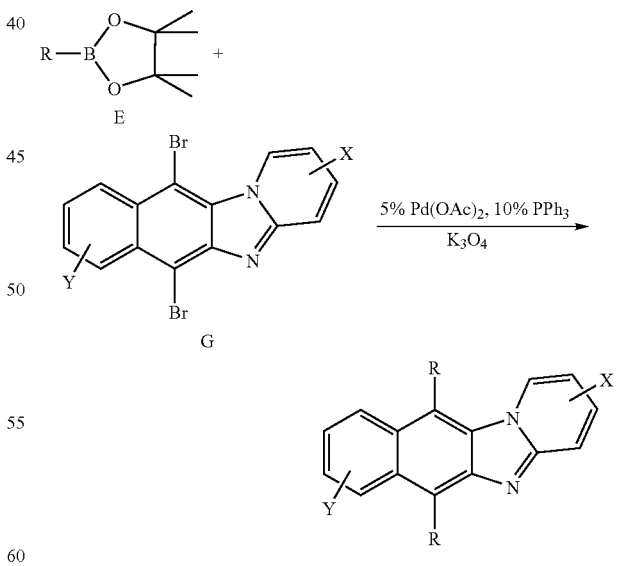

wherein R is selected from the group consisting of a substituted or unsubstituted alkyl group, substituted or unsubstituted alkenyl group, substituted or unsubstituted aryl group, substituted or unsubstituted heterocyclic group, and substituted or unsubstituted alicyclic group, and M is halogen.

Then, the compound E may be allowed to react with the compound G using Suzuki coupling according to Reaction Scheme 5 so as to prepare the inventive compound:

wherein X and Y are each independently selected from the group consisting of hydrogen, a substituted or unsubstituted alkyl group, substituted or unsubstituted alkenyl group, substituted or unsubstituted aryl group, substituted or unsubstituted heterocyclic group, substituted or unsubstituted alicyclic group, and substituted or unsubstituted silicon group. Each of X and Y may be at least two in number, in which case these substituents X or Y can be different from each other. Also, in Reaction Scheme 2, R is $R^1$ or $R^2$ in Formula 1 or 2 and is selected from the group consisting of hydrogen, a substituted or unsubstituted alkyl group, substituted or unsubstituted alkoxy group, substituted or unsubstituted alkenyl group, substituted or unsubstituted aryl group, substituted or unsubstituted arylamine group, substituted or unsubstituted heterocyclic group, substituted or unsubstituted alicyclic group, substituted or unsubstituted silicon group, substituted or unsubstituted boron group, amino group, nitrile group, nitro group, halogen group, amide group, and ester group. Preferably, it is a substituted or unsubstituted aryl group, substituted or unsubstituted arylamine group, substituted or unsubstituted heterocyclic group, or substituted or unsubstituted alkenyl group. In Reaction Scheme 2 above, $R^1$ and $R^2$ may be different from each other, but are preferably the same substituents.

In another embodiment of the present invention, the inventive compounds can be prepared in the following manner. First, the compound B prepared according to Reaction Scheme 1 may be allowed to react according to Reaction Scheme 3 below to prepare compounds F and G.

[Reaction Scheme 5]

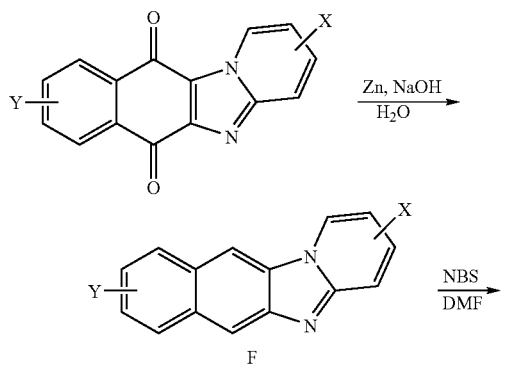

F wherein R, X and Y have the same meanings as defined above in Reaction Schemes 1, 2 and 4. In Reaction Scheme 5, R is $R^1$ or $R^2$ in Formula 1 or 2, and $R^1$ and $R^2$ may be different from each other, but are preferably the same substituents.

The organic electronic device according to the present invention can be fabricated using conventional methods and materials for fabricating organic electronic devices, except that the above-described compounds are used to form at least one organic layer. Hereinafter, an organic light-emitting device will be illustrated.

In one embodiment of the present invention, the organic light-emitting device may have a structure comprising a first electrode, a second electrode and an organic layer interposed therebetween, and can be fabricated using a conventional method and materials for fabricating organic light-emitting devices, except that the inventive compound is used in at least one organic layer in the organic light-emitting device. The structure of the organic light-emitting device according to the present invention is illustrated in FIG. 1.

For example, the organic light-emitting device according to the present invention can be fabricated by depositing metal, conductive metal oxide or an alloy thereof on a substrate using a PVD (physical vapor deposition) process such as sputtering or e-beam evaporation so as to form an anode on the substrate, forming thereon organic layers, including a hole injection layer, hole transport layer, light-emitting layer and electron transport layer, and then depositing thereon a material which can be used as a cathode. In addition to this method, the organic light-emitting device can also be made by sequentially depositing a cathode material, an organic layer structure and an anode material on a substrate (see International Patent Application Publication No. WO2003/012890).

The organic layer structure may be a multilayer structure comprising a hole injection layer, hole transport layer, light-emitting layer and electron transport layer, but is not limited thereto, and may also be a single-layer structure. Also, the organic layer structure can be formed to have a reduced number of layers using various polymer materials through a solvent process other than the vapor deposition process, for example, a spin coating process, dip coating process, doctor blading process, screen printing process, inkjet printing process, or thermal transfer process.

The anode material is preferably a material which has a high work function so as to make it easy to inject holes into the organic layer. Specific examples of the anode material, which can be used in the present invention, include, but are not limited to, metals such as vanadium, chromium, copper, zinc and gold, or alloys thereof; metal oxides such as zinc oxide, indium oxide, indium tin oxide (ITO) and indium zinc oxide (IZO); combinations of metal and oxide, such as ZnO:Al and $SnO_2$:Sb; and conductive polymers such as poly(3-methylthiophene), poly[3,4-(ethylene- 1,2-dioxy)thiophene](PEDT), polypyrrole and polyaniline.

The cathode material is preferably a material which has a low work function so as to make it easy to inject electrons into the organic layers. Specific examples of cathode material that can be used in the present invention include, but are not limited to, metals such as magnesium, calcium, sodium, potassium, titanium, indium, yttrium, gadolinium, aluminum, silver, tin and lead, or alloys thereof; and multilayer structure materials such as LiF/Al and $LiO_2$/Al.

As for the hole injection material, it is preferable to use a material that can receive holes from the anode well at low voltage, and has a HOMO (highest occupied molecular orbital) between the work function of the anode material and the HOMO of the surrounding organic layers. Specific examples of hole injection material that can be used in the present invention include metal porphyrine, oligothiophene, arylamine-based organic material, hexanitrile hexaazatriphenylene, quinacridone-based organic material, perylene-based organic material, anthraquinone, and polyaniline-based and polythiophene-based conductive polymers, but are not limited thereto.

As for the hole transport material, it is preferable to use a material which can transfer holes from the anode or the hole injection layer to the light-emitting layer, and which has high hole mobility. Specific examples thereof include, but are not limited to, arylamine-based organic material, conductive polymers, and block copolymers having both conjugated portions and non-conjugated portions.

As for the light-emitting material, it is preferable to use a material which can emit light in the visible spectrum by readily receiving holes and electrons from the hole transport layer and the electron transport layer, respectively, and recombining the received holes and electrons with each other, and has good quantum efficiency for fluorescence or phosphorescence. Specific examples thereof include, but are not limited to, 8-hydroxyquinoline aluminum complex ($Alq_3$); carbazole-based compounds; dimerized styryl compounds; BAlq; 10-hydroxybenzoquinoline-metal compounds; compounds of benzoxazole, benzothiazole and benzimidazole series; polymers based on poly-phenylenevinylene (PPV); spiro compounds; and polyfluorene and rubrene.

As for the electron transport material, it is preferable to use a material which can transfer electrons from the cathode to the light-emitting layer, and which has high electron mobility. Specific examples thereof include, but are not limited to, aluminum complex of 8-hydroxyquinoline; complex including $Alq_3$; organic radical compounds; hydroxyflavone-metal complex.

The organic light-emitting structure according to the present invention may have a top emission structure, a bottom emission structure or a top and bottom emission structure according to the kind of material used.

The compounds according to the present invention can also act in organic electronic devices, including organic solar cells, organic photoconductors and organic transistors, according to a principle similar to the principle applicable to the organic light-emitting device.

BEST MODE

Figure 1:
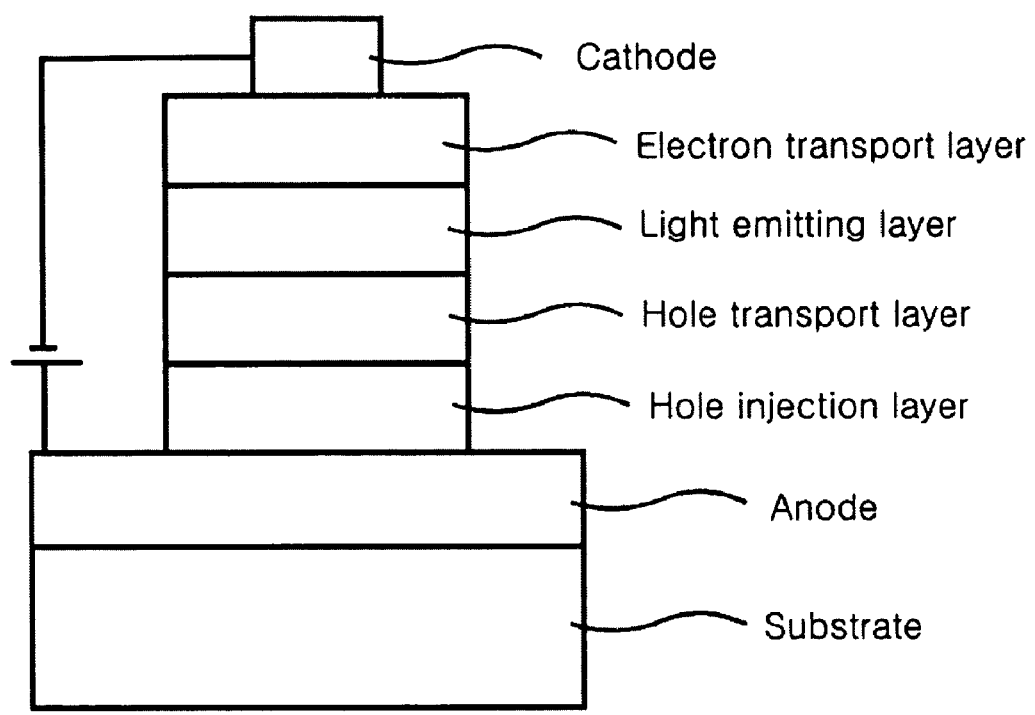
FIG. 1 illustrates the structure of an organic light-emitting device according to one embodiment of the present invention.
Figure 2:
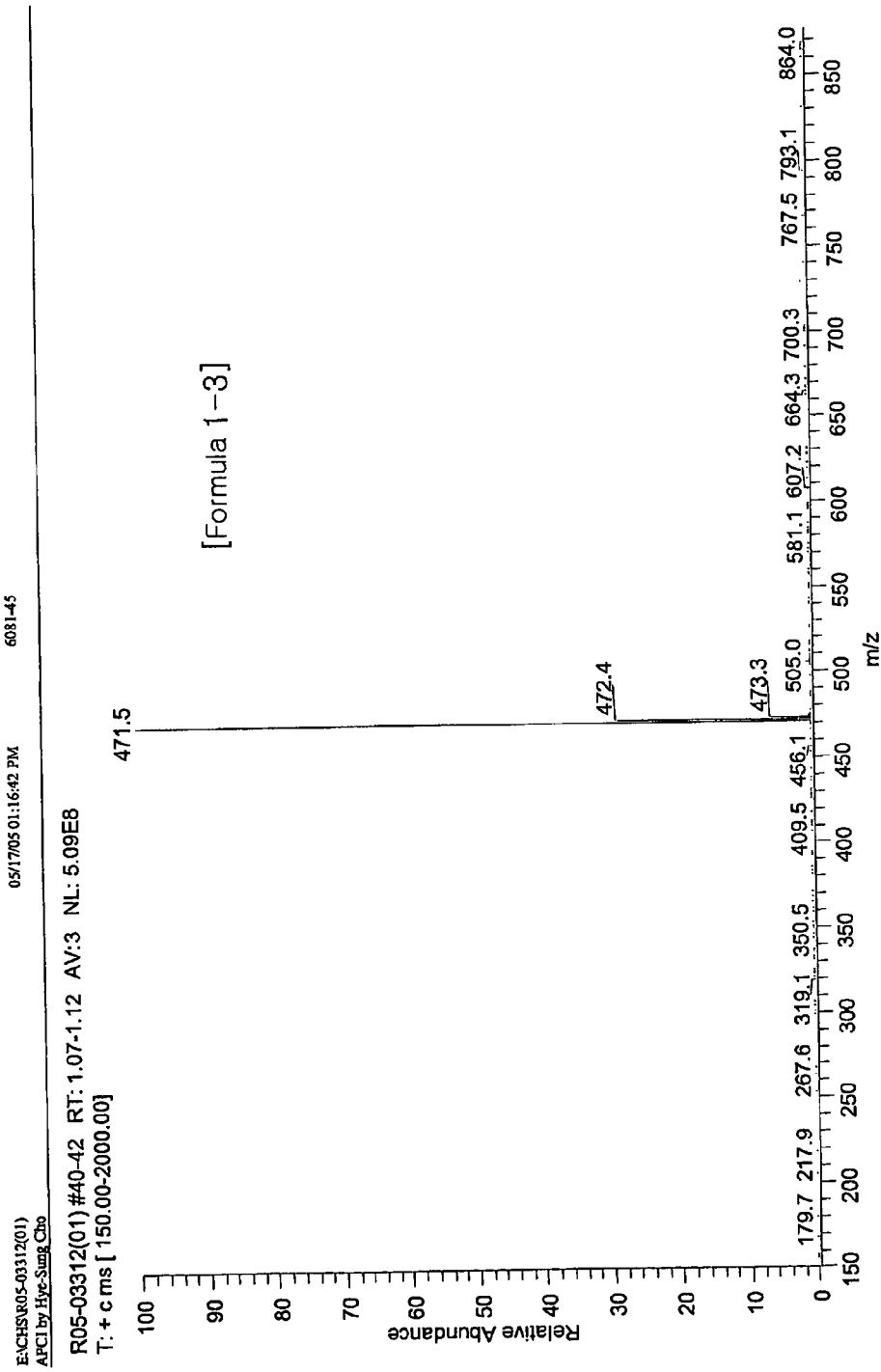
FIG. 2 shows the MS spectrum of the compound of Formula 1-3 according to the present invention.
Figure 3:
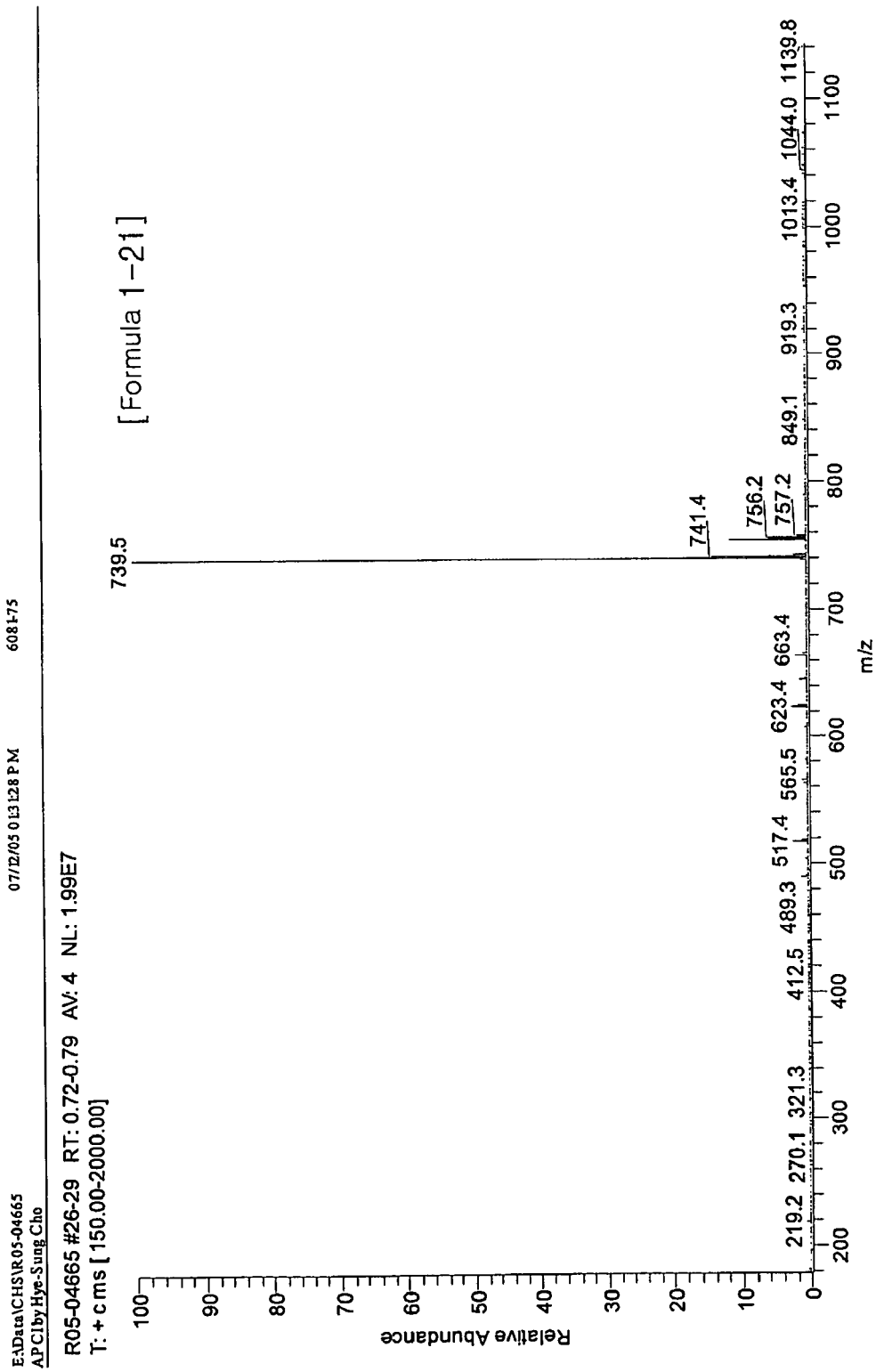
FIG. 3 shows the MS spectrum of the compound of Formula 1-21 according to the present invention.
Figure 4:
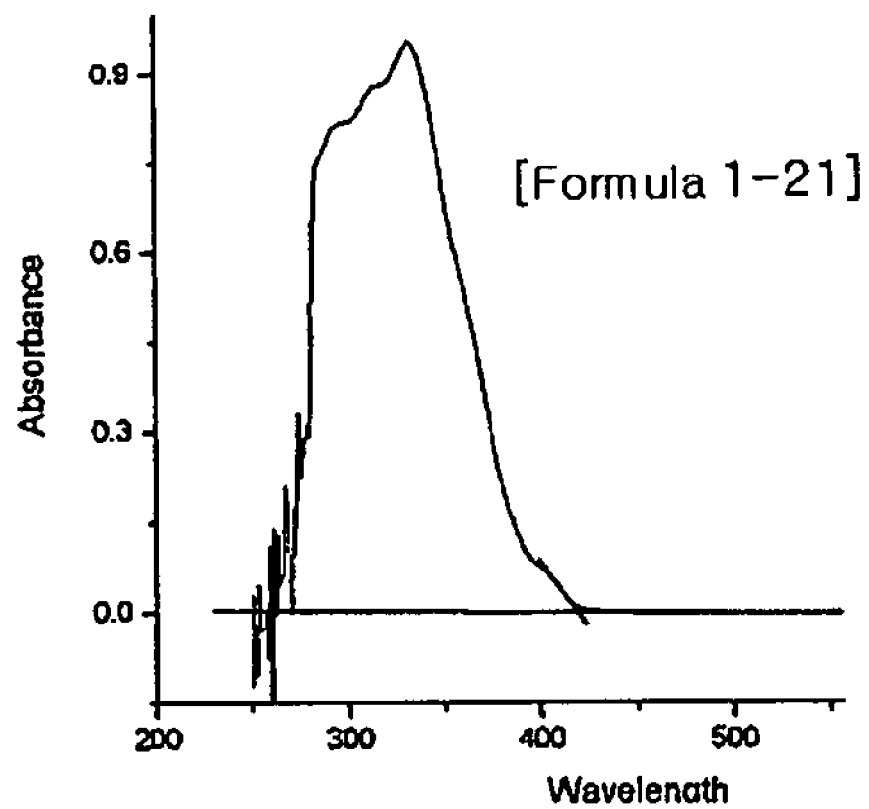
FIG. 4 shows the UV spectrum of the compound of Formula 1-21 according to the present invention.

Hereinafter, the present invention will be described in further detail with reference to Preparation Examples and Test Examples. It is to be understood, however, that these examples are not to be construed to limit the scope of the present invention.

EXAMPLES 1

Preparation of Compound of Formula 1-3

1. Preparation of Compound 3B

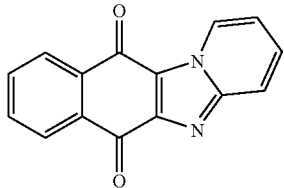

2.5 g (8.0 mmol) of 2,3-dichloro-1,4-naphthoquinone and 1.0 g (10.7 mmol) of 2-aminopyridine were dissolved in 11 ml of ethanol (EtOH) and heated and stirred for 4 hours. The reaction solution was then added to 40 ml of acetic acid without further purification, and heated and stirred for 2 hours. After lowering the reaction temperature to room temperature, the formed precipitate was separated through filtration, yielding 1.5 g (65% yield) of the compound 3B (X and Y=H).

MS [M+H]$^+$=249

2. Preparation of Compound 3C

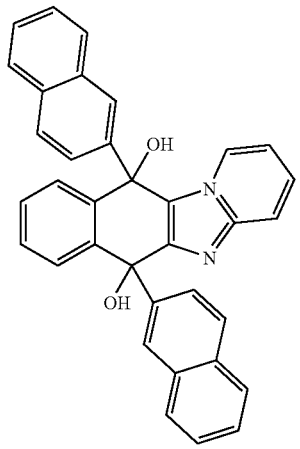

3.06 g (14.8 mmol) of 2-bromonaphthalene was dissolved in 140 ml of tetrahydrofuran. Then, the solution was cooled to −78° C., and 10.4 ml (17.7 mmol) of a 1.7 M solution of t-BuLi (t-butyl lithium) in hexane was slowly added thereto using a syringe, followed by stirring for 1 hour. To the stirred solution, 1.48 g (5.9 mmol) of the compound 3B (X and Y=H) prepared in said step 1 was added and the mixture was warmed to room temperature and stirred for 5 hours. After the reaction was terminated with a saturated ammonium chloride solution, the reaction product was extracted with tetrahydrofuran (20 ml×2), dried with anhydrous magnesium sulfate and then filtered under reduced pressure. The filtrate was evaporated under reduced pressure to remove the solvent, and the residue was heated and stirred in toluene (20 ml) for 2 hours. After cooling to room temperature, the formed precipitate was filtered under reduced pressure, yielding 1.63 g (56% yield) of the compound 3C.

MS [M+H]$^+$=505

3. Preparation of Compound of Formula 1-3

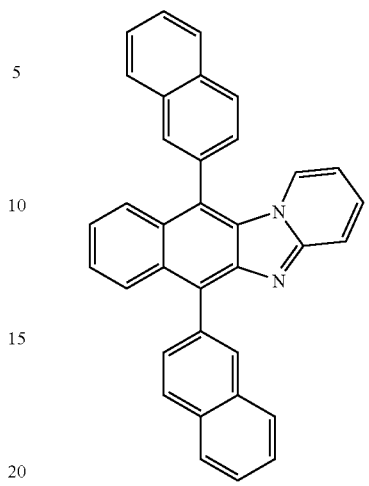

1.63 g (3.2 mmol) of the compound 3C (X and Y=H, and R=naphthalene), 1.61 g (9.6 mmol) of potassium iodide (KI) and 2.05 g (19.3 mmol) of sodium hypophosphite (NaH$_2$PO$_2$.H$_2$O) were added to acetic acid (32 ml), and the solution was heated and stirred for 5 hours. After cooling to room temperature, the precipitate was filtered under reduced pressure. The precipitate was added to tetrahydrofuran (20 ml), 1 N NaOH solution (20 ml) was added thereto, and the mixture was stirred for 1 hour. The stirred solution was extracted with tetrahydrofuran (20 ml×2) and then dried with anhydrous magnesium sulfate (MgSO$_4$), followed by filtration. The filtrate solution was evaporated under reduced pressure to remove the solvent, yielding 2.0 g (80% yield) of the compound of Formula 1-3.

MS [M+H]$^+$=471.

EXAMPLE 2

Another Method for Preparing Compound of Formula 1-3

1. Preparation of Compound 3E (R=2-naphthyl Group in Compound E of Reaction Scheme 4)

1.3 g (6.27 mmol) of 2-bromonaphthalene, 33.4 mg (0.19 mmol) of palladium chloride (PdCl$_2$) and 98.6 mg (0.38 mmol) of triphenyl phosphine (PPh$_3$) were dissolved in dioxane (20 ml), and then 2.62 ml (18.8 mmol) of triethylamine (NEt$_3$) and 1.36 ml (9.4 mmol) of 4,4,5,5-tetramethyl-1,3,2-dioxaborolane were added thereto. After heating to 80° C., the mixture solution was stirred for 6 hours. After cooling to room temperature, water and brine were added to the reaction mixture, and then the reaction product was extracted with ethyl ether (20 ml×2). The extracted material was dried with anhydrous magnesium sulfate and then filtered under reduced pressure, and the solvent was removed under reduced pressure. Recrystallization yielded the compound 3E (R=2-naphthyl group in compound E of Reaction Scheme 4).

2. Preparation of Compound 3F (X and Y=H in Compound F of Reaction Scheme 3)

To 20 g of activated zinc, 165 ml of distilled water, 24.8 g of sodium hydroxide (NaOH) and 3.0 g (12.1 mmol) of the compound B (X and Y=H) were added, and the mixture solution was heated and stirred for 24 hours. After cooling to room temperature, the stirred solution was filtered through celite, and the filtrate was extracted with dichloromethane (50 ml×3), dried with anhydrous magnesium sulfate and then filtered under reduced pressure. The filtrate was evaporated under reduced pressure to remove the solvent, and the residue was recrystallized with ethyl ether and hexane, yielding 1.5 g (58% yield) of the compound 3F (X and Y=H).

3. Preparation of Compound 3G (X and Y=H in Compound G of Reaction Scheme 3)

1.5 g (6.0 mmol) of compound F (X and Y=H) and 3.1 g (17.2 mmol) of NBS (N-bromosuccinimide) were dissolved in 70 ml of dimethylformamide (DMF) and then stirred at room temperature for 40 minutes. The formed precipitate was filtered under reduced pressure, yielding 2 g (77% yield) of the compound 3G (X and Y=H).

4. Preparation of Compound of Formula 1-3

68 mg (0.3 mmol) of palladium acetate (Pd(OAc)$_2$), 158 mg (0.6 mmol) of triphenylphosphine (PPh$_3$), 6.6 mmol of the compound 3E and 3.82 g (18 mmol) of tripotassium phosphate (K$_3$PO$_4$) were dissolved in 20 ml of tetrahydrofuran (THF), and 3.38 g (9 mmol) of the compound 3G was added thereto. After heating to 80° C., the mixture solution was stirred for 24 hours, cooled to room temperature and then recrystallized, yielding the desired compound of Formula 1-3.

EXAMPLE 3

Preparation of Compound of Formula 1-18

1. Preparation of Compound 18B-1

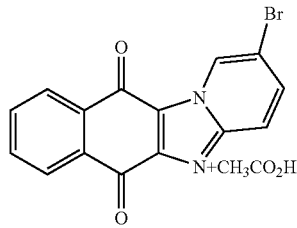

5 g (15.9 mmol) of 2,3-dichloro-1,4-naphthoquinone and 5.47 g (31.6 mmol) of 2-amino-5-bromopyridine were dissolved in 100 ml of ethanol (EtOH), and the solution was heated and stirred for 16 hours. After cooling to room temperature, 50 ml of 4N HCl solution was added to the reaction solution, and the mixture solution was heated and stirred for 5 hours. After cooling to room temperature, the precipitate was filtered, sufficiently washed with water, and then dried, yielding 5.4 g (88.6% yield) of an acetate of the compound 18B-1.

MS [M+H]$^+$=327(Br×1)

2. Preparation of Compound 18B-2

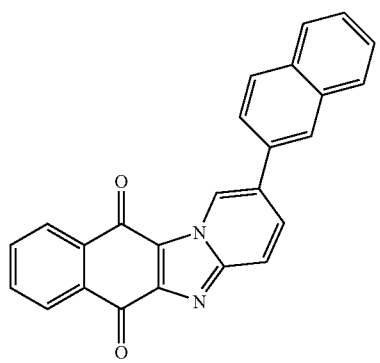

4 g (12.2 mmol) of the acetate of the compound 18B-1 was heated and stirred for 16 hours without further purification together with 2.1 g (12.2 mmol) of naphthylboronic acid, 0.7 g (0.61 mmol) of Pd(PPh$_3$)$_4$, 100 ml of 2 M K$_2$CO$_3$ solution and 100 ml of THF solution. After lowering the reaction temperature to room temperature, the formed solid was filtered, sufficiently washed with water and ethanol and then dried, yielding 3.74 g (82% yield) of the compound 18B-2 as an intermediate compound.

MS [M+H]$^+$=375

3. Preparation of Compound 18C (X=2-naphthyl Group, Y=H, R=2-naphthyl Group in Compound C of Reaction Scheme 2)

5.48 g (87% yield) of the compound 18C was prepared in the same manner as in the section 2 of Example 1, except that the compound 18B-2 prepared in said section 2 was used in place of the compound 3B.

MS [M+H]$^+$=631

4. Preparation of Compound of Formula 1-18

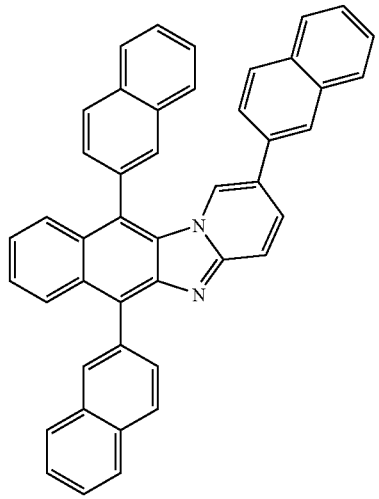

4.3 g (83% yield) of the compound of Formula 1-18 was prepared in the same manner as in the section 3 of Example 1, except that the compound 18C prepared in said section 3 was used in place of the compound 3C.

MS [M+H]$^+$=597

EXAMPLE 4

Preparation of Compound of Formula 1-21

1. Preparation of Compound 21B-1

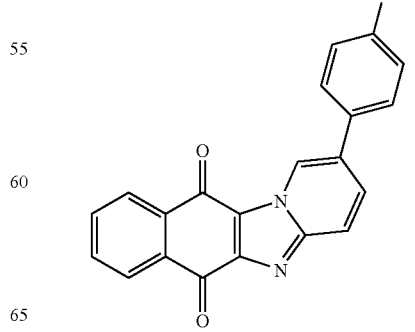

The compound 21B-1 was prepared in the same manner as in the section 2 of Example 3, except that 4-formylphenylboronic acid was used in place of 2-naphthylboronic acid.

MS [M+H]$^+$=353

2. Preparation of Compound 21B-2

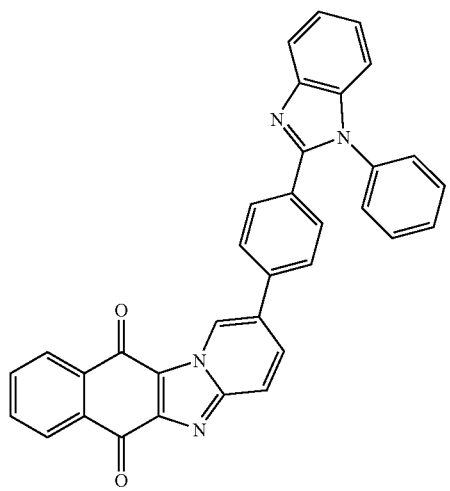

3.9 g (11 mmol) of the compound 21B-1, 2 g (11 mmol) of N-phenyl-1,2-phenylenediamine and 60 ml of N,N-dimethylacetamide were mixed with each other and heated at 160° C. for 10 hours. After removing the solvent under reduced pressure, the reaction product was stirred in 100 ml of ethanol, thus obtaining 3.4 g (56% yield) of the compound 21B-2 as a yellow solid.

MS [M+H]$^+$=517

3. Preparation of Compound 21C

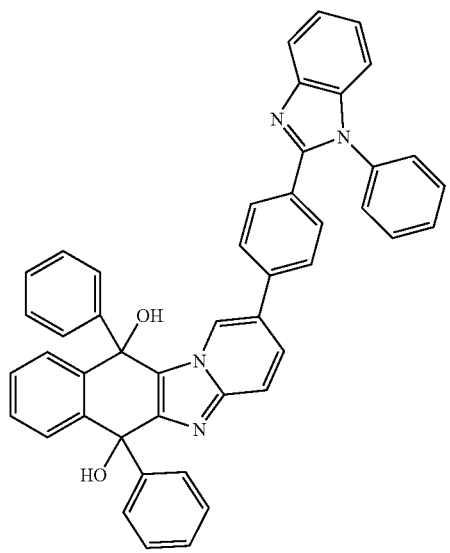

4.8 g (92% yield) of the compound 21C was prepared in the same manner as in section 2 of Example 1, except that the compound 21B-2 prepared in said section 2 was used in place of the compound 3B.

MS [M+H]$^+$=673.

4. Preparation of Compound of Formula 1-21

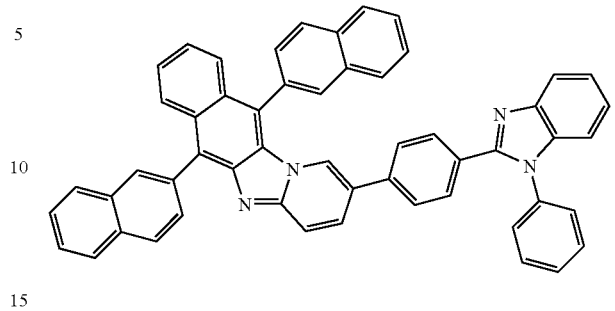

2.7 g (67% yield) of the compound of Formula 1-21 was prepared in the same manner as in section 3 of Example 1, except that the compound 21C prepared in said section 3 was used in place of the compound 3C.

MS [M+H]$^+$=739.

TEST EXAMPLE 1

A glass substrate having a thin film of ITO (indium tin oxide) coated thereon to a thickness of 1500 Å was immersed in distilled water having a detergent dissolved therein, and was ultrasonically washed. Herein, as the detergent, a product commercially available from Fischer Co. was used, and as for the distilled water, distilled water filtered two times through a filter manufactured by Millipore Co. was used. The ITO was washed for 30 minutes and then ultrasonically washed two times with distilled water for 10 minutes. After completion of the distilled water washing, the substrate was ultrasonically washed with a mixed solvent of isopropyl alcohol, acetone and methanol, dried and then transported into a plasma cleaner. Also, the substrate was cleaned using oxygen plasma for 5 minutes and then transported into a vacuum evaporator.

On the ITO transparent electrode thus prepared, hexanitrile hexaazatriphenylene was thermally deposited in a vacuum to a thickness of 500 Å, thus forming a hole injection layer. On the hole injection layer, hole transport material NPB was deposited in a vacuum to a thickness of 400 Å, and then an Alq$_3$ compound was deposited in a vacuum to a thickness of 300 Å thus forming a light-emitting layer.

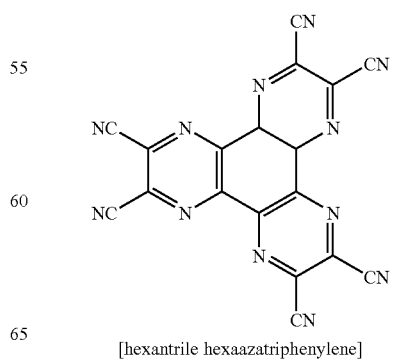

[hexantrile hexaazatriphenylene]

-continued

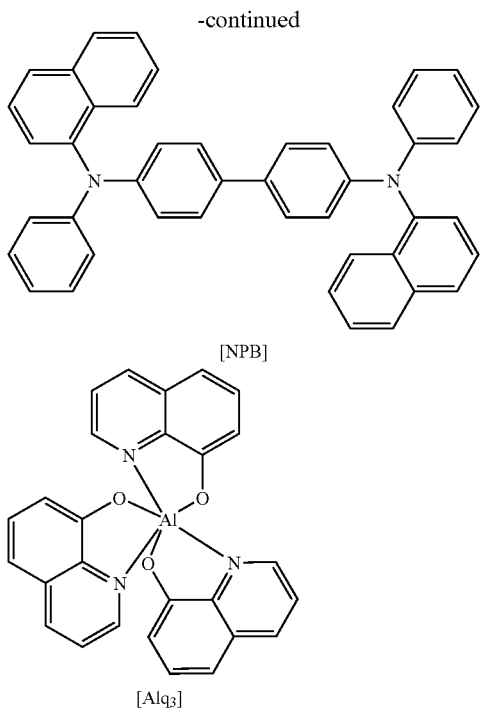

[NPB]

[Alq₃]

On the light-emitting layer, the compound of Formula 1-3 prepared in Example 1, was deposited in a vacuum to a thickness of 200 Å thus forming an electron injection and transport layer. On the electron injection and transport layer, 5 Å thick lithium fluoride (LiF) and 2500 Å thick aluminum were sequentially deposited, thus forming a cathode.

In the above procedures, the deposition rate of the organic materials was maintained at 1 Å/sec, the deposition rate of lithium fluoride was maintained at 0.2 Å/sec, and the deposition of aluminum at 3-7 Å/sec.

A forward electric field of 6.6 V was applied to the above-fabricated organic light-emitting device and, as a result, green light corresponding to x=0.33 and y=0.56 on the basis of the 1931 CIE color coordinate was observed at a current density of 50 mA/cm². Also, a forward electric field of 7.16 V was applied and, as a result, green light having an efficiency of 2.7 cd/A was observed at a current density of 100 mA/cm².

TEST EXAMPLE 2

On the ITO electrode prepared as described in Test Example 1 above, hexanitrile hexaazatriphenylene (500 Å), 4,4'-bis[N-(1-naphthyl)-N-phenylamino]biphenyl (NPB) (400 Å), the compound (200 Å) of Formula 1-3 prepared in Example 1, and Alq₃ (300 Å), were sequentially thermally deposited in a vacuum, thus forming a hole injection layer, hole transport layer, light-emitting layer and electron transport layer, respectively. On the electron transport layer, 12 Åthick lithium fluoride (LiF) and 2000 Åthick aluminum were sequentially deposited, thus forming a cathode. An organic light-emitting device was fabricated in this way.

A forward electric field of 5.6 V was applied to the above-fabricated organic light-emitting device and, as a result, blue light corresponding to x=0.18 and y=0.24 on the basis of the 1931 CIE color coordinates was observed at a current density of 50 mA/cm². Also, a forward electric field of 9.96 V was applied and, as a result, blue light having an efficiency of 2.1 cd/A was observed at a current density of 100 mA/cm².

TEST EXAMPLE 3

On the ITO electrode prepared as described in Test Example 1 above, hexanitrile hexaazatriphenylene (500 Å), 4,4'-bis[N-(1-naphthyl)-N-phenylamino]biphenyl (NPB) (400 Å), Alq₃ (300 Å), and the compound (200 Å) of Formula 1-21 prepared in Example 3, were sequentially thermally deposited in a vacuum, thus forming a hole injection layer, hole transport layer, light-emitting layer and electron transport layer, respectively. On the electron transport layer, 12 Å thick lithium fluoride (LiF) and 2000 Å thick aluminum were sequentially deposited, thus forming a cathode. An organic light-emitting device was fabricated in this way.

A forward electric field of 6.3 V was applied to the above-fabricated organic light-emitting device and, as a result, green light corresponding to x=0.32 and y=0.55 on the basis of the 1931 CIE color coordinates was observed at a current density of 50 mA/cm². Also, a forward electric field of 8.65 V was applied and, as a result, green light having an efficiency of 4.6 cd/A was observed at a current density of 100 mA/cm².

The conditions and results of Test Examples 1 to 3 above were shown in Table 1.

TABLE 1

| Test Example No. | Material (use) | Tg (° C.) | Voltage (V at 100 mA) | cd/A (at 100 mA) |
|---|---|---|---|---|
| Comparative Example 1 | Alq₃ | 165 | 9.5 | 4.8 (green) |
| Test Example 1 | Formula 1-3 | N.D | 7.16 | 2.7 (green) |
| Test Example 2 | Formula 1-3 | N.D | 9.96 | 2.1 (blue) |
| Test Example 3 | Formula 1-21 | 238 | 8.65 | 4.6 (green) |

INDUSTRIAL APPLICABILITY

The inventive compounds are novel compounds, which can perform the role of hole injection, hole transport, light emission, or electron injection and/or transport in organic electronic devices, including organic light-emitting devices, and also can serve as a light-emitting host together with a suitable dopant. When the inventive compounds are applied to organic electronic devices, including organic light-emitting devices, these can achieve excellent effects in terms of the efficiency, driving voltage and stability of the devices.

The invention claimed is:

1. An organic electronic device comprising a first electrode, a second electrode and one or more organic layers disposed between the first and second electrodes, in which at least one layer of the organic layers comprises a compound represented by Formula 1:

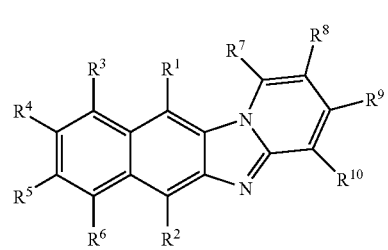

[Formula 1]

wherein R¹ to R¹⁰ are each independently or together selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted alicyclic group, a substituted or unsubstituted silicon group, a substituted or unsubstituted boron group, an amino group, a nitrile group, a nitro group, a halogen group, an amide group, and an ester group, wherein two substituents adjacent to each other may form an alicyclic or heterocyclic ring together.

2. The organic electronic device of claim 1, wherein the organic layers comprise an electron injection and transport layer comprising the compound of Formula 1.

3. The organic electronic device of claim 1, wherein the organic layers comprise a light-emitting layer comprising the compound of Formula 1.

4. The organic electronic device of claim 1, wherein the organic layers comprise a hole transport layer comprising the compound of Formula 1.

5. The organic electronic device of claim 1, wherein the organic layers comprise a layer of performing all of electron injection, electron transport, and light emission, the layer comprising the compound of Formula 1.

6. The organic electronic device of claim 1, which the organic electronic device is selected from the group consisting of organic light-emitting devices, organic solar cells, organic photoconductors (OPC) and organic transistors.

7. An imidazole derivative represented by Formula 2:

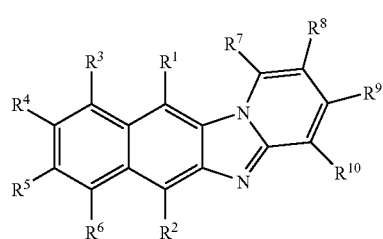

[Formula 2]

wherein $R^1$ to $R^{10}$ are each independently or together selected from the group consisting of hydrogen, a substituted or unsubstituted alkyl group, a substituted or unsubstituted alkoxy group, a substituted or unsubstituted alkenyl group, a substituted or unsubstituted aryl group, a substituted or unsubstituted arylamine group, a substituted or unsubstituted heterocyclic group, a substituted or unsubstituted alicyclic group, a substituted or unsubstituted silicon group, a substituted or unsubstituted boron group, an amino group, a nitrile group, a nitro group, a halogen group, wherein two substituents adjacent to each other may form an alicyclic or heterocyclic ring together, provided that all of $R^1$ to $R^{10}$ are not simultaneously hydrogen.

8. The imidazole derivative of claim 7, wherein $R^1$ and $R^2$ are not simultaneously hydrogen and are each independently selected from hydrogen, a substituted or unsubstituted alkenyl group, a substituted or unsubstituted aryl group, a substituted or unsubstituted arylamine group, and a substituted and unsubstituted heterocyclic group, $R^3$ to $R^6$ are each independently selected from the group consisting of hydrogen, a nitrile group, a substituted or unsubstituted aryl group, a substituted or unsubstituted arylamine group, and a substituted or unsubstituted heterocyclic group, and $R^7$ to $R^{10}$ are each independently selected from the group consisting of hydrogen, a nitrile group, an alkyl group, a substituted or unsubstituted alkenyl group, a substituted or unsubstituted aryl group, a substituted or unsubstituted arylamine group, and a substituted or unsubstituted heterocyclic group.

9. The imidazole derivative of claim 7, wherein $R^1$ and $R^2$ are selected from the group consisting of an alkenyl group, aryl group, arylamine group and heterocyclic group, $R^3$ to $R^6$ are hydrogen, and $R^7$ to $R^{10}$ are selected from the group consisting of hydrogen, a nitrile group, alkyl group, alkenyl group, aryl group, arylamine group and heterocyclic group.

10. The imidazole derivative of claim 7, wherein the compound of Formula 2 is selected from the group consisting of compounds represented by the following formulas:

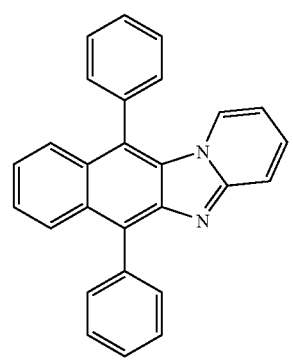

[Formula 1-1]

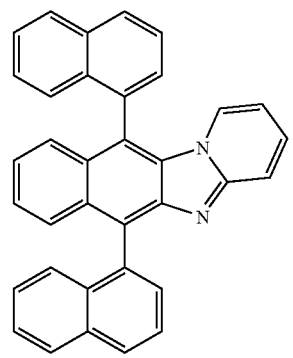

[Formula 1-2]

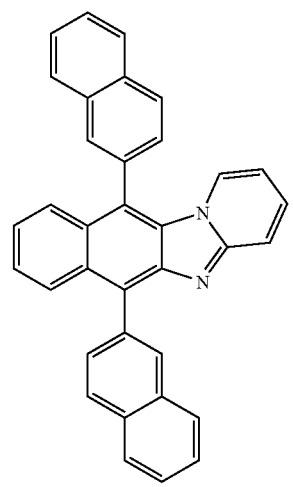

[Formula 1-3]

[Formula 1-4]
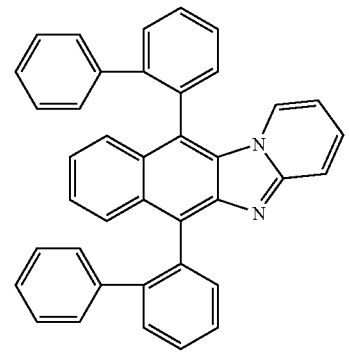
[Formula 1-5]
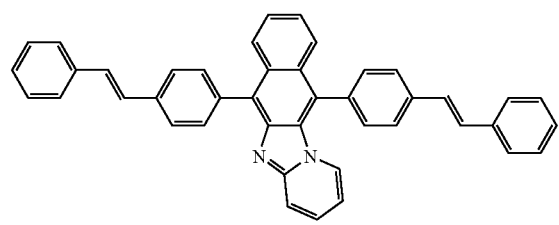
[Formula 1-6]
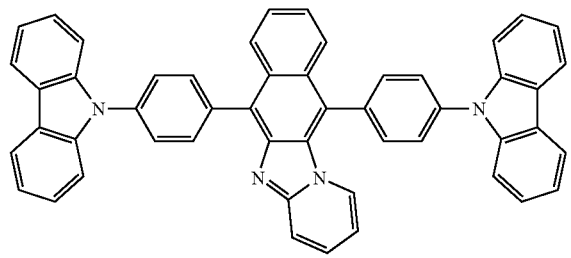
[Formula 1-7]
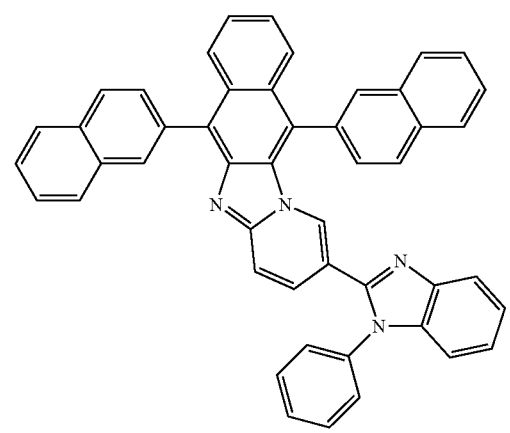
[Formula 1-8]
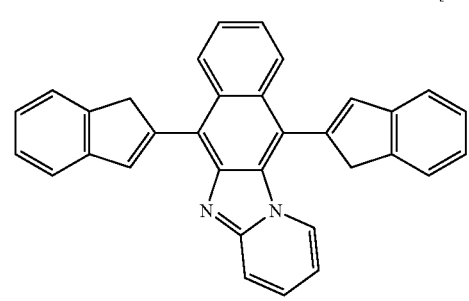
[Formula 1-9]
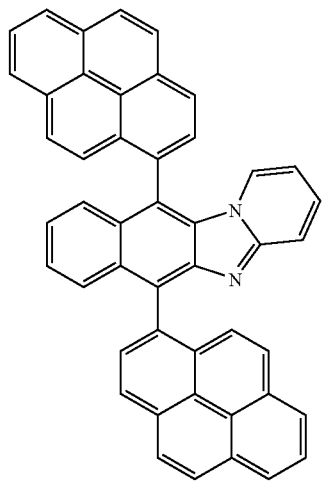
[Formula 1-10]
[Formula 1-11]
[Formula 1-12]
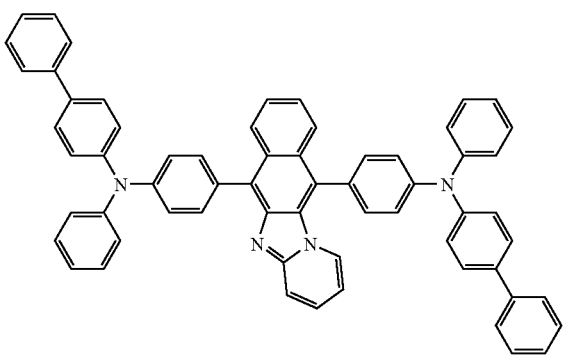

-continued
[Formula 1-13]
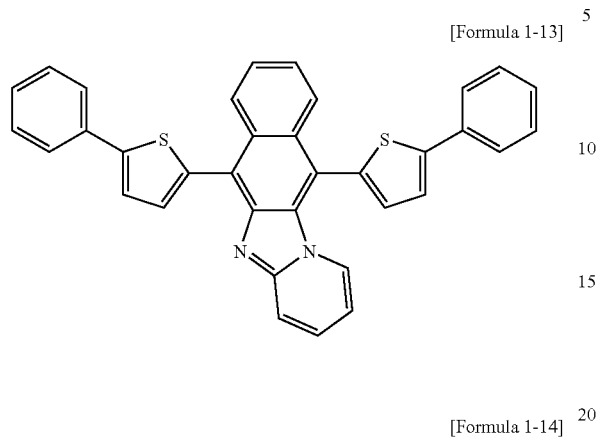
[Formula 1-14]
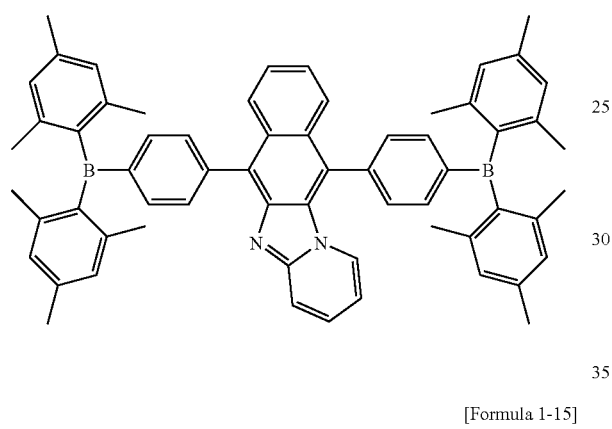
[Formula 1-15]
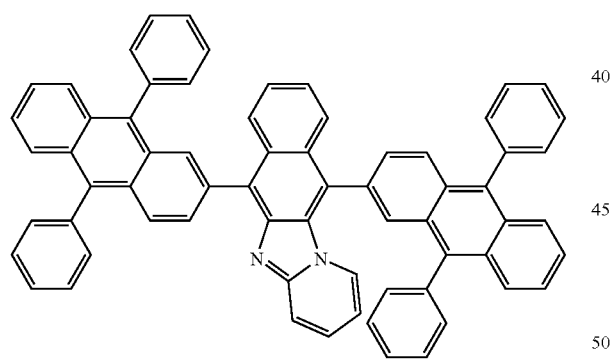
[Formula 1-16]
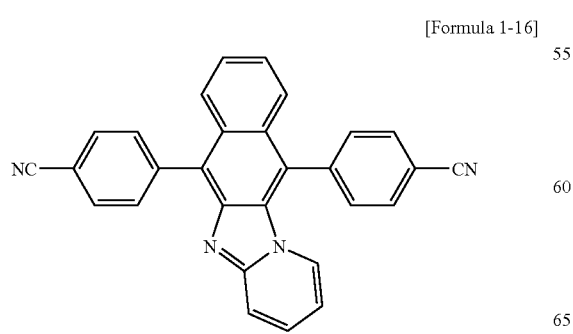
-continued
[Formula 1-17]
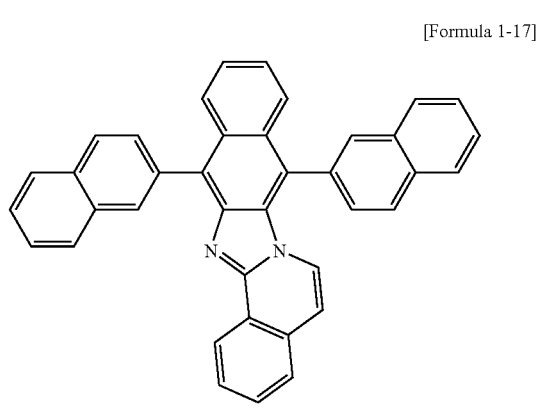
[Formula 1-18]
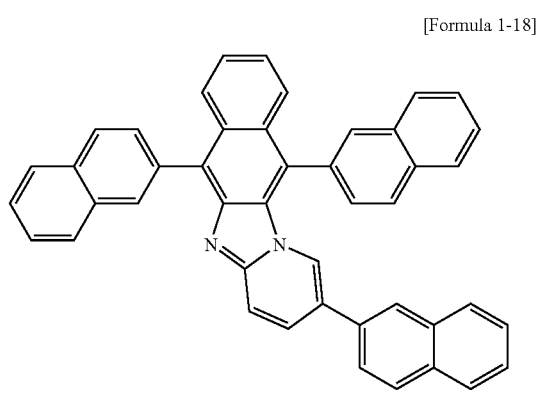
[Formula 1-19]
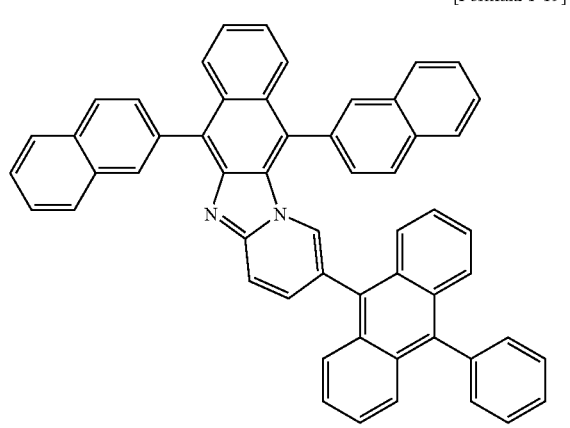

[Formula 1-20]
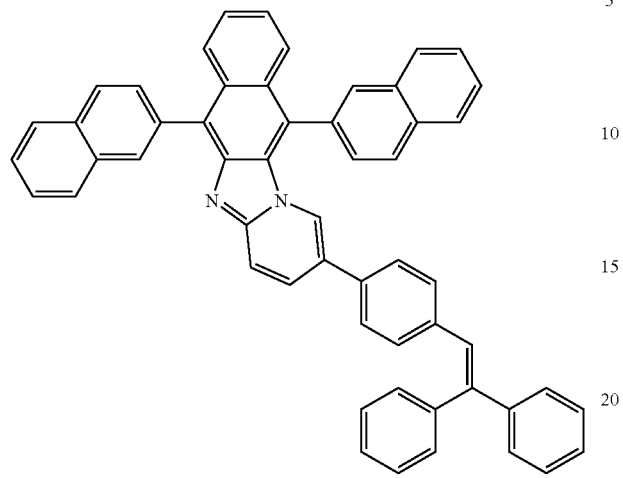
[Formula 1-23]
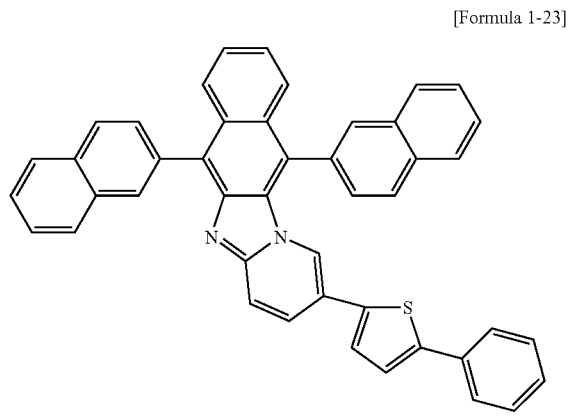
[Formula 1-21]
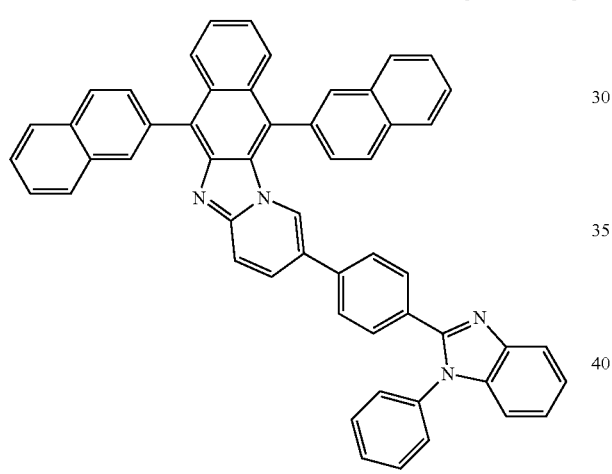
[Formula 1-24]
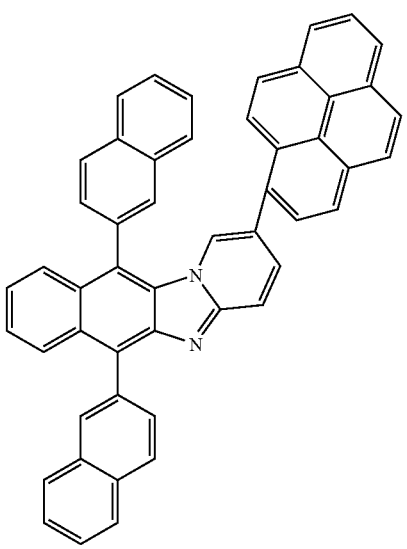
[Formula 1-22]
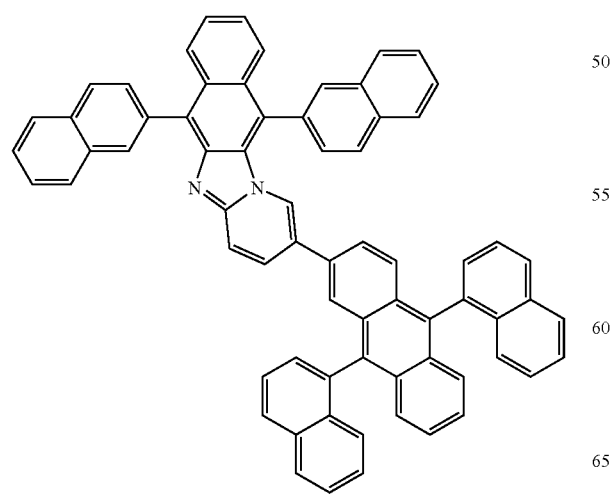
[Formula 1-25]
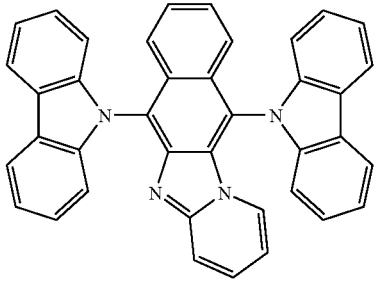

-continued
[Formula 1-26]
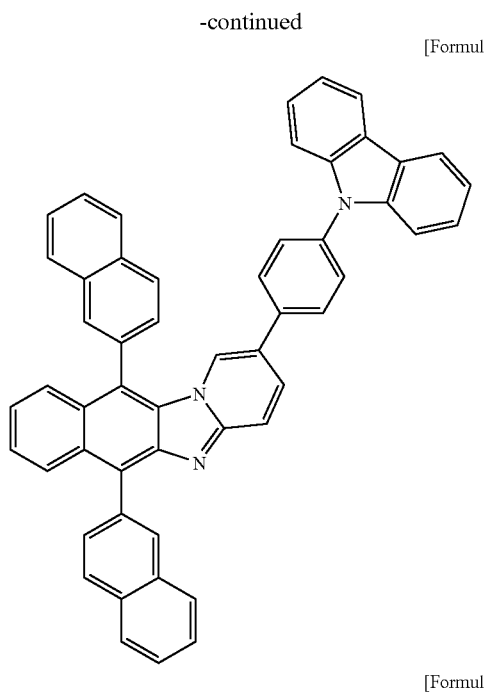
[Formula 1-27]
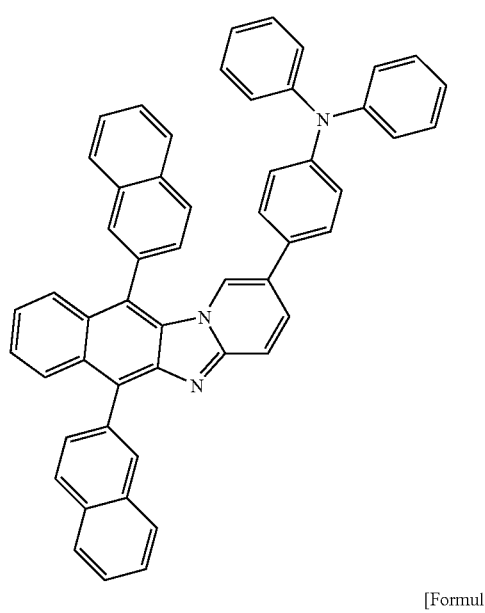
[Formula 1-28]
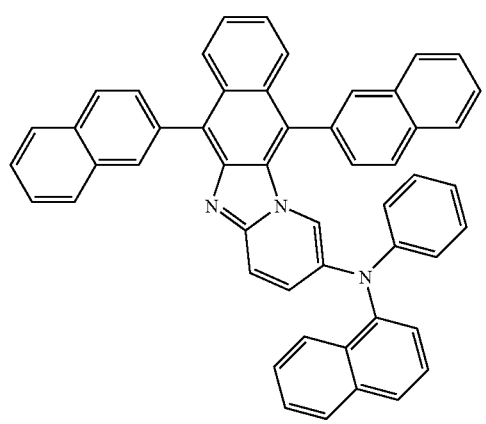
-continued
[Formula 1-29]
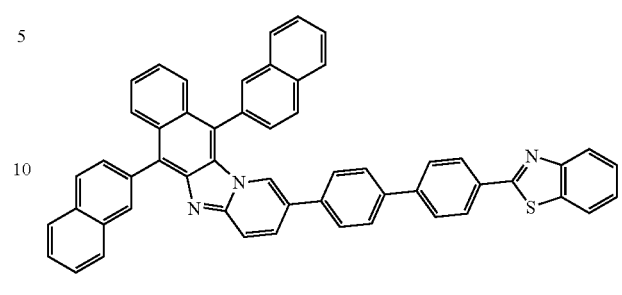
[Formula 1-30]
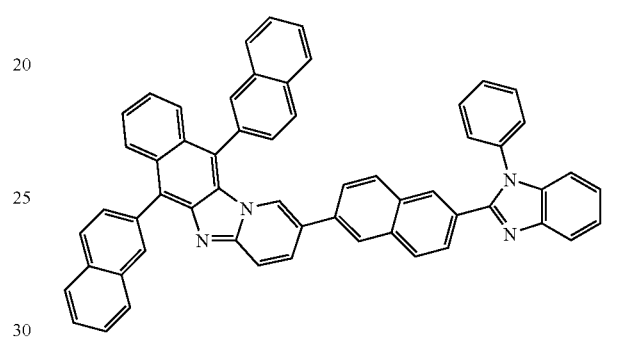
[Formula 1-31]
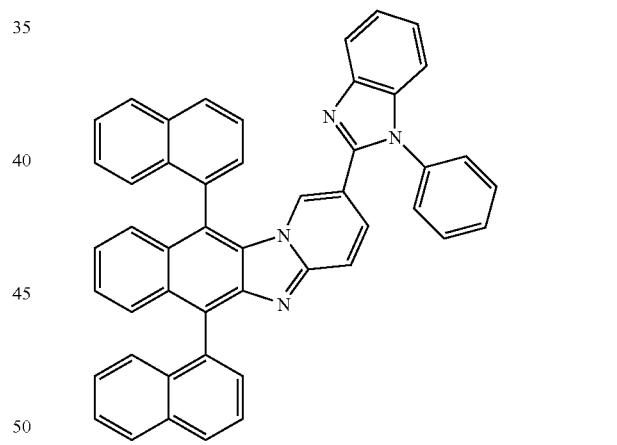
[Formula 1-32]
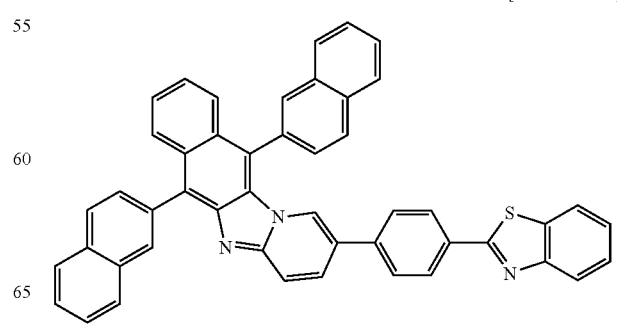

-continued
[Formula 1-33]
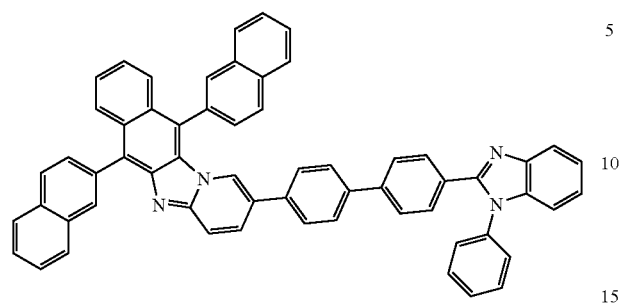
[Formula 1-34]
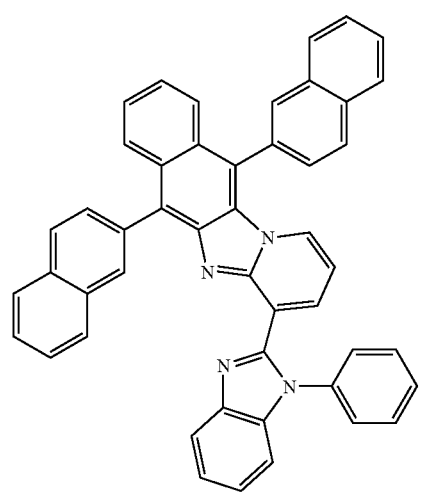
[Formula 1-35]
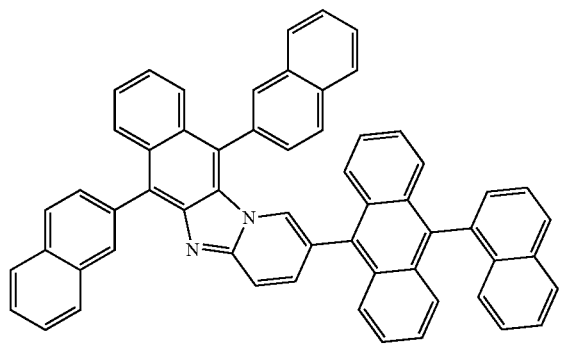
[Formula 1-36]
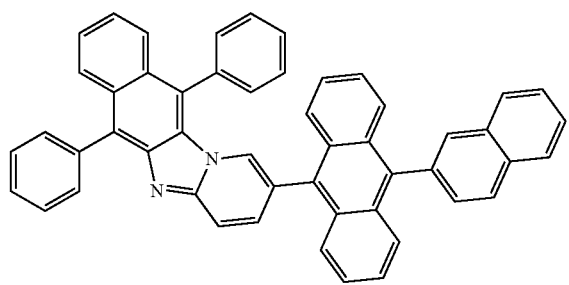
-continued
[Formula 1-37]
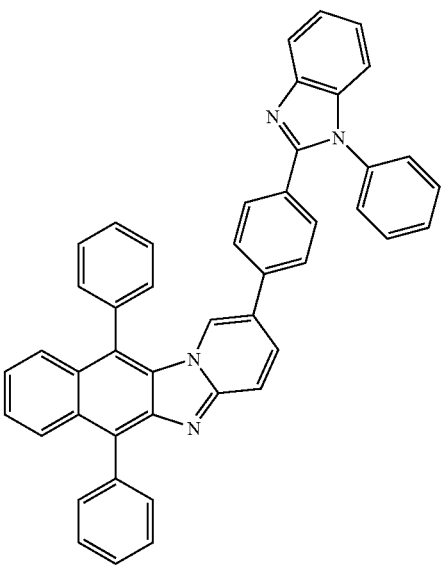
[Formula 1-38]
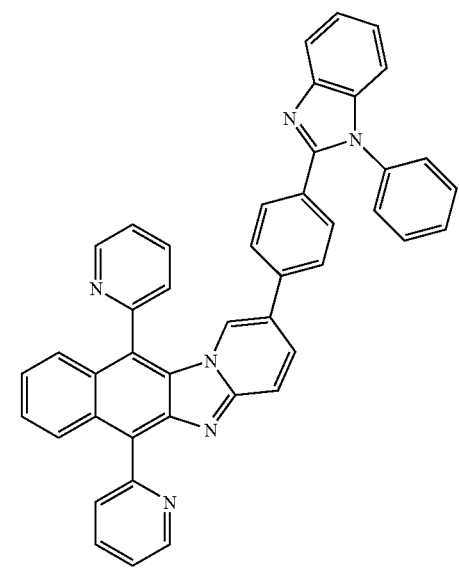
[Formula 1-39]
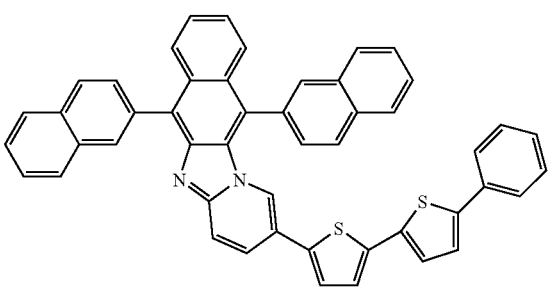

-continued
[Formula 1-40]
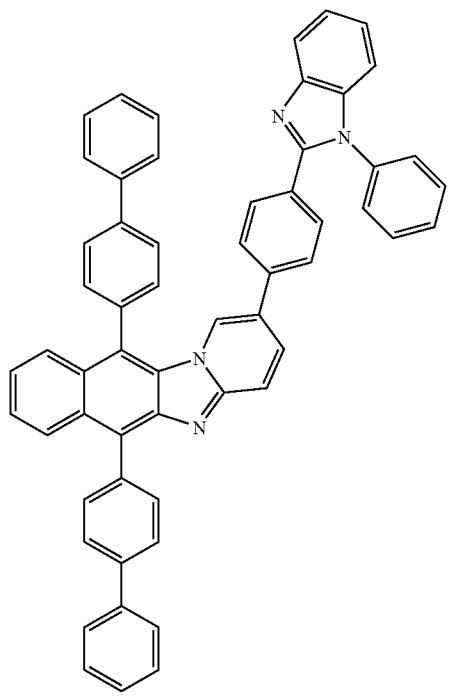
[Formula 1-41]
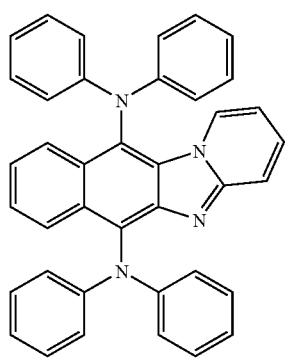
[Formula 1-42]
[Formula 1-43]
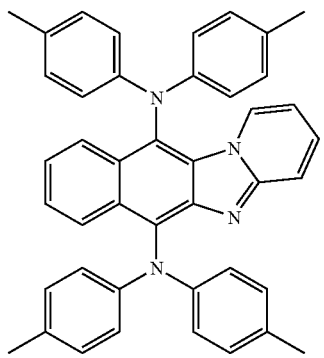
[Formula 1-44]
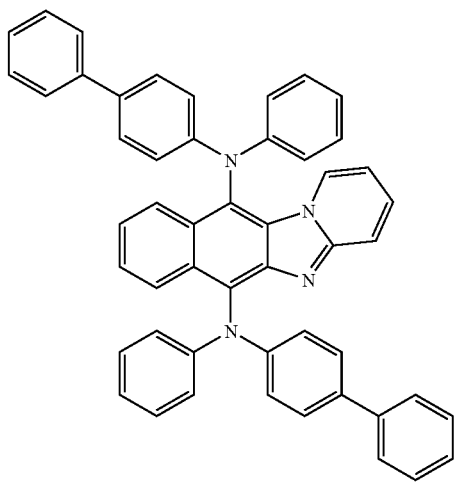
[Formula 1-45]
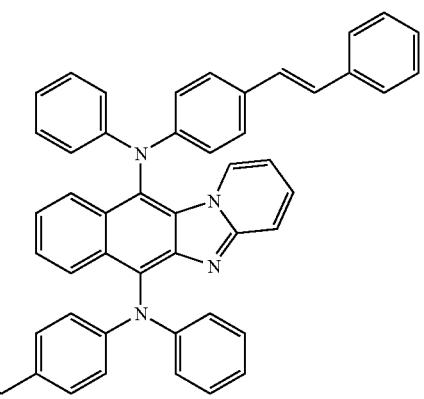

-continued

[Formula 1-46]

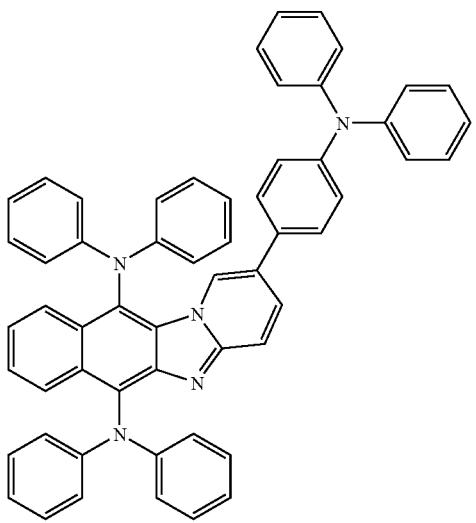

[Formula 1-47]

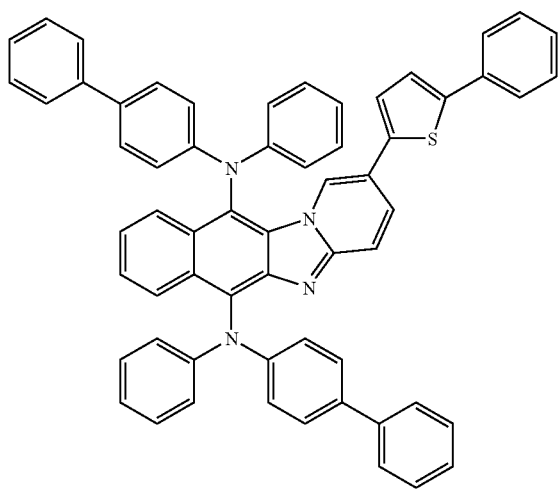

11. A method for preparing an imidazole derivative set forth in claim 7, comprising the steps of:

a) allowing substituted or unsubstituted 2,3-dihalogen-1,4-naphthoquinone to react with a substituted or unsubstituted ortho-aminopyridine derivative;

b) converting the ketone group of the compound obtained in said step a) into alcohol so as to prepare a dialcohol compound; and c) reducing the dialcohol compound obtained in said step b) to produce a naphthalene group in the compound.

12. A method for preparing an imidazole derivative set forth in claim 7, comprising the steps of:

a) allowing substituted or unsubstituted 2,3-dihalogen-1,4-naphthoquinone to react with a substituted or unsubstituted ortho-aminopyridine derivative;

b) reducing the naphthoquinone group of the compound obtained in said step a) to produce a naphthalene group;

c) introducing bromine (Br) into each of positions to be substituted with $R^1$ and $R^2$ in the compound obtained in said step b); and d) using boronic acid or borate to introduce substituents into the positions introduced with the bromo group in the compound obtained in said step c).

* * * * *